US012805785B2

(12) United States Patent
Maggi

(10) Patent No.: US 12,805,785 B2
(45) Date of Patent: Nov. 24, 2026

(54) BLACK SILICON-BASED NANOPATTERNED ELECTRODES

(71) Applicant: Ecate LLC, Los Angeles, CA (US)

(72) Inventor: Alessandro Maggi, Los Angeles, CA (US)

(73) Assignee: ECATE LLC, Los Angeles, CA (US)

( * ) Notice: Subject to any disclaimer, the term of this patent is extended or adjusted under 35 U.S.C. 154(b) by 150 days.

(21) Appl. No.: 18/932,426

(22) Filed: Oct. 30, 2024

(65) Prior Publication Data

US 2025/0134407 A1 May 1, 2025

Related U.S. Application Data

(60) Provisional application No. 63/594,955, filed on Nov. 1, 2023, provisional application No. 63/594,373, filed on Oct. 30, 2023.

(51) Int. Cl.

| | |
|---|---|
| ***A61B 5/263*** | (2021.01) |
| ***A61B 5/00*** | (2006.01) |
| ***A61B 5/20*** | (2006.01) |
| ***B81B 1/00*** | (2006.01) |
| ***B81C 1/00*** | (2006.01) |

(52) U.S. Cl.

CPC .............. *A61B 5/263* (2021.01); *A61B 5/204* (2013.01); *A61B 5/6874* (2013.01); *B81B 1/008* (2013.01); *B81C 1/00111* (2013.01); *A61B 2562/028* (2013.01); *A61B 2562/0285* (2013.01); *B81B 2201/055* (2013.01); *B81C 2201/0132* (2013.01)

(58) Field of Classification Search

CPC ..... B81B 2203/04; A61B 5/262; A61B 5/263; A61B 5/265; A61B 5/268

See application file for complete search history.

(56) References Cited

U.S. PATENT DOCUMENTS

| | | | | |
|---|---|---|---|---|
| 9,867,979 B2 * | 1/2018 | Saini | ...................... | A61B 5/297 |
| 2009/0192569 A1 * | 7/2009 | Llinas | .................... | A61B 5/293 607/45 |
| 2010/0065946 A1 * | 3/2010 | Wilson | ................ | B81C 1/00952 438/459 |
| 2012/0012967 A1 * | 1/2012 | Jiang | ................... | H10F 30/2275 257/E31.066 |
| 2016/0208110 A1 * | 7/2016 | Kim | .................... | C09D 5/1681 |
| 2018/0086633 A1 * | 3/2018 | Somaschini | ........... | G02B 5/003 |

FOREIGN PATENT DOCUMENTS

| | | | | | |
|---|---|---|---|---|---|
| CN | 102117850 | A | * | 7/2011 | |
| CN | 111586958 | A | * | 8/2020 | ............... H05H 1/46 |
| JP | 2575206 | B2 | * | 1/1997 | |
| KR | 20120016308 | A | * | 2/2012 | ............ H10P 50/242 |
| TW | 1725765 | B | * | 4/2021 | ......... H10F 39/8063 |

* cited by examiner

*Primary Examiner* — Eun Hwa Kim

(74) *Attorney, Agent, or Firm* — SEYFARTH SHAW LLP

(57) ABSTRACT

A sensor is described. The sensor includes a nano-patterned semiconductor layer on a frontside of a substrate. The sensor also includes a frontside conductive layer on the nano-patterned semiconductor layer on the frontside of the substrate. The sensor further includes a backside conductive layer on a backside of the substrate, distal from the frontside conductive layer.

14 Claims, 16 Drawing Sheets

360

380

930
M1
922
904
902

940
R
A
M2
M1
922
R
M2
942
904
902

950
960
R
A
M2
M1
922
R
M2
942
904

900
904
902

910
912
904
902

920
922

BLACK SILICON-BASED NANOPATTERNED ELECTRODES

CROSS-REFERENCE TO RELATED APPLICATIONS

The present application claims the benefit of U.S. Provisional Patent Application No. 63/594,373, filed Oct. 30, 2023, and titled "BLACK SILICON-BASED NANOPATTERNED MICRO-ELECTRODES FOR NEURAL STIMULATION," and U.S. Provisional Patent Application No. 63/594,955, filed Nov. 1, 2023, and titled "BLACK SILICON-BASED NANO-PATTERNED SURFACE ELECTRODES FOR BLADDER VOLUME ACUTE AND CHRONIC MONITORING," the disclosures of which are expressly incorporated by reference herein in their entireties.

TECHNICAL FIELD

The present disclosure generally relates to fabrication of sensing and stimulating electrodes. More specifically, the present disclosure relates to the design and fabrication of nano-patterned electrodes for sensing and stimulation.

BACKGROUND

Tissue stimulation was first achieved during the 1960s and has resulted in the commercialization of several life-saving therapies, especially in the cardiac environment. Additionally, neural stimulation has experienced tremendous success, leading to revolutionizing treatments, such as deep brain stimulation (DBS) for Parkinson's disease, spinal cord stimulation for chronic pain reduction, sacral nerve stimulation to induce bladder and bowel voiding in paralyzed people are a few examples. In recent years the neurotech space has seen dramatic advancements targeted toward the development of high-bandwidth, bi-directional brain machine interfaces (BMI) and brain computer interfaces (BCI). A great amount of effort is devoted to neural sensing while stimulation has been traditionally labeled as a mature and known technique. Unfortunately, the need for spatially selective, stable, and safe stimulation involves technology that is not yet fully developed. Additionally, conventional implanted devices utilized for stimulation experience significant issues related to implant anchoring, power consumption, transmission rates, and pressure measurement accuracy which, over time, render implanted devices inadequate for chronic use.

SUMMARY

A sensor is described. The sensor includes a nano-patterned semiconductor layer on a frontside of a substrate. The sensor also includes a frontside conductive layer on the nano-patterned semiconductor layer on the frontside of the substrate. The sensor further includes a backside conductive layer on a backside of the substrate, distal from the frontside conductive layer.

A sensor is described. The sensor includes a nano-patterned semiconductor layer on a portion of a frontside of the substrate. The sensor also includes a first conductive layer on the nano-patterned semiconductor layer on the portion of the frontside of the substrate. The sensor further includes a second conductive layer on the first conductive layer. The sensor further also includes second conductive layer on the substrate surrounding the nano-patterned semiconductor layer on the portion of the frontside of the substrate.

This has outlined, rather broadly, the features and technical advantages of the present disclosure in order that the detailed description that follows may be better understood. Additional features and advantages of the disclosure will be described below. It should be appreciated by those skilled in the art that this disclosure may be readily utilized as a basis for modifying or designing other structures for carrying out the same purposes of the present disclosure. It should also be realized by those skilled in the art that such equivalent constructions do not depart from the teachings of the disclosure as set forth in the appended claims. The novel features, which are believed to be characteristic of the disclosure, both as to its organization and method of operation, together with further objects and advantages, will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following description taken in conjunction with the accompanying drawings.

DETAILED DESCRIPTION

Figure 1B:
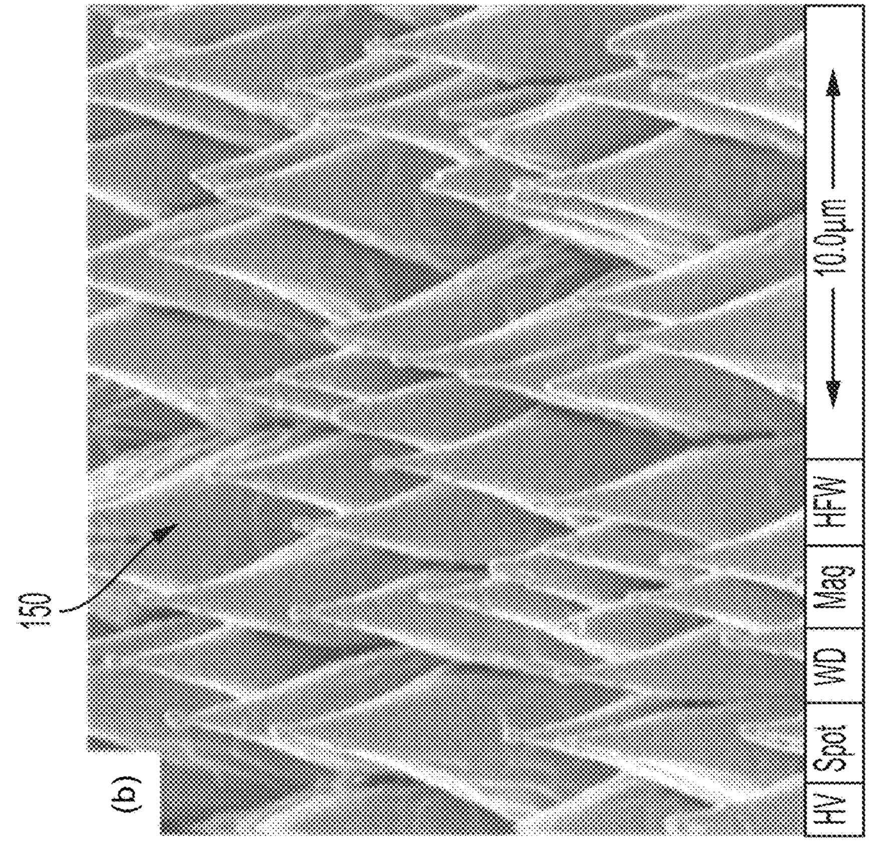
FIG. 1B is a scanning electron microscope (SEM) image of dense conical black silicon (BSi) features, coated in a layer of high pressure sputtered conductive material, according to various aspects of the present disclosure.

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. It will be apparent, however, to those skilled in the art that these concepts may be practiced without these specific details. In some instances, well-known structures and components are shown in block diagram form in order to avoid obscuring such concepts.

As described herein, the use of the term "and/or" is intended to represent an "inclusive OR," and the use of the term "or" is intended to represent an "exclusive OR." As described herein, the term "exemplary" used throughout this description means "serving as an example, instance, or illustration," and should not necessarily be construed as preferred or advantageous over other exemplary configurations. The term "coupled" used throughout this description means "connected, whether directly or indirectly through intervening connections (e.g., a switch), electrical, mechanical, or otherwise," and is not necessarily limited to physical connections. Additionally, the connections can be such that the objects are permanently connected or releasably connected.

Incontinence is a major problem that affects millions of people. A subset of this patient population involves spinal cord injury (SCI) patients who have lost control over their bladder. In SCI patients, incontinence can lead to urinary infections which are one of the primary causes of hospitalization in this patient population. Current solutions are largely unsatisfactory. Bladder status monitoring is crucial to provide an effective treatment, however no long-term solution has been developed yet.

Problems related to biofouling, signal drift, power consumption, and signal degradation over time constitute the main hurdles to the development of a long-term effective bladder status monitoring device.

Various aspects of the present disclosure are directed to nano-patterned surface electrodes that can be implanted on the detrusor muscle to monitor a bladder volume status. In some implementations, the nano-patterned surface electrodes are composed of black silicon (BSi) of different density and dimensions coated with a conductive material. The nano-patterned surface electrodes exhibit a drastically reduced electrode impedance, which enables electrode miniaturization leading to a reduction in tissue inflammation and ensuing foreign body response, which enables this approach amenable for chronic bladder status monitoring.

Additionally, tissue stimulation was first developed in the 1960s and resulted in the commercialization of several life-saving therapies, especially in the cardiac environment. Neural stimulation has also experienced tremendous success, leading to revolutionizing treatments such as deep brain stimulation (DBS) for Parkinson's disease, spinal cord stimulation for chronic pain reduction, sacral nerve stimulation to induce bladder and bowel voiding in paralyzed people are a few examples. In recent years, the neurotech space has seen dramatic advancements targeted toward the development of high-bandwidth, bi-directional brain machine (BMI) and brain computer interfaces (BCI). A great amount of effort has been devoted to neural sensing, while stimulation has been traditionally labeled as a mature and known technique. Unfortunately, the need for spatially selective, stable and safe stimulation involves technology that is not yet fully developed.

In particular, a solution applicable to both bladder volume monitoring as well as spinal cord stimulation is desired. Various aspects of the present disclosure are directed to restoring sensation of bladder fullness in spinal cord injury (SCI) patients. Restoring the sensation of bladder fullness in SCI involves (1) knowing when the bladder is full and (2) stimulating the correct area of the patient's spinal cord for the patient to feel that their bladder is full. In some implementations, nano patterning of electrodes reduces biofouling and extends the life of the electrodes, which can accurately monitor bladder volume chronically (e.g., over several years).

Additionally, various aspects of the present disclosure stimulate specific regions of the white matter of the spinal cord (e.g., the dorsolater funiculus) for the patient to feel a specific sensation; namely, the urge to urinate. In particular, spatially selective stimulation is specified; otherwise, the patient feels a range of sensations. For instance, instead of just the urge to urinate, the patient might feel pressure on their legs, pain, heat, etc. One significant issue associated with spatially selective stimulation is electrode size. For example, the smaller the electrode, the higher spatial resolution/selectivity; however, smaller electrodes exhibit high impedance, which may lead to possible tissue and electrode damage during stimulation.

Various aspects of the present disclosure perform nano-patterning of electrodes with black silicon, which drastically increases the electrode surface area while decreasing the impedance. In this implementation, the nano-patterning of electrodes decreases the electrode size while maintaining an impedance at relatively reduced value for avoiding tissue/electrode damage during stimulation.

Various aspects of the present disclosure circumvent these note limitations by nanopatterning the stimulating and reference electrodes, leading to a dramatic decrease in electrode impedance ($Z_e$) and increasing a charge density capability (CDC) due to the larger available surface area. In some implementations, nanopatterning of the stimulating and reference electrodes utilizes black silicon (BSi), which is a surface modification of silicon that exhibits high levels of surface roughness as a result of extremely dense, high-aspect ratio (AR) nano-strands formed from the surface modification.

Additionally, various aspects of the present disclosure recognize the native functional organization of the spinal cord and utilize custom-made nanopatterned electrodes, which improve signal-to-noise ratio, charge injection, and electrode stability over time. In practice, the white matter in the spinal cord communicates with the brain in one-dimension and is characterized by a fractured somatotopy in which representations of motor and sensory activity of the body are discretely and spatially organized in axon bundles. The collection of these axon bundles holds all the motor and sensory information that is being exchanged between the body and the brain. As a result of this intrinsic map and compactness of information within the spinal cord, stimulation of target areas becomes simpler and a reduced number of electrodes is specified to restore sensation to a significant portion (e.g., over 90%) of the body, making spinal cord machine interfaces the best candidate for developing neural interfaces capable of restoring both sensation and motor control in paralyzed people.

Volume Change Detection via Tissue Impedance Monitoring

Currently bladder status is generally measured acutely using catheter-based sensors which are inserted directly through the urethra into the bladder to monitor pressure variations. This methodology is bulky and can potentially lead to urinary tract infections (UTI), therefore it is not suitable for prolonged use. Several types of implantable pressure sensors based on microelectromechanical systems (MEMS) technology have been developed; however, issues related to implant anchoring, power consumption, transmission rates, and pressure measurement accuracy over time have made them inadequate for chronic use.

An alternative route that has been explored aside from pressure sensing involves volume sensing. The basic principle of operation behind volume sensing revolves around bladder wall thinning during bladder filling. As the bladder fills up with urine it stretches causing the bladder wall impedance to increase at specific frequencies. For example, changes in a bladder wall impedance can be detected when the impedance is measured from a predetermined range (e.g., ~0.5-100 kHz) and these changes tend to be more difficult to measure outside this frequency range.

Traditionally this change is detected by means of suturing two flat electrodes on the detrusor muscle and measuring the impedance between the two. This technique was successful in acute environments (<2 weeks) but was abandoned due to encapsulation of these electrodes by fibrotic tissue which led to the need for constant recalibration, rendering it unfeasible for long term clinical applications.

Upon electrode insertion, the body responds by depositing proteins, small molecules and cells in a process called biofouling which eventually passivates and potentially encapsulates the implant. Biofouling causes an increase in electrode impedance which is one of the major causes of implant failure and has been the center of much research devoted to drastically reduce it.

Limitations of the noted-conventional solutions include: (1) biofouling, (2) electrode mechanical stability, (3) signal drift, and (4) power limitations. In particular, past attempts to detect bladder volume by means of surface electrodes are implemented by wrapping wires around the bladder, which consumes significant areas (e.g., >1 $cm^2$) leading to a significant foreign body response. A strong foreign body response causes excessive fibrosis around the sensing electrodes leading to the need for frequent recalibrations and possibly device failure due to an excessive increase in electrode impedance, which results in the noted biofouling.

Additionally, large metallic wires or cuff-type electrodes that are wrapped around the bladder needed to be sutured on the bladder, which caused severe tissue inflammation. This severe tissue inflammation leads to electrode encapsulation over time or electrode delamination from the bladder muscle (detrusor), which results in the noted electrode mechanical instability.

Several wireless methods are employed for monitor changes in bladder volume or pressure. Most of these methods involve power and signal transfer via coupled coils. Inductor-capacitor (LC) tank circuits are commonly employed to establish communication between the outside and inside of the body; however, such communication involves a minimum relative movement of one coil with respect to the other coil, which is maintained over time to enable the communication. The bladder's large and somewhat non-consistent movements over micturition cycles makes this route impractical for chronic monitoring, which results in the noted signal drift issue.

Another solution involves ultrasonic monitoring of bladder volume. Unfortunately, ultrasonic monitoring of bladder volume involves a bulky, expensive device that is impractical for everyday use outside the hospital. More importantly, literature has raised concerns over the significant amount of energy (e.g., >100 $mW/cm^2$) that would be specified for continuous monitoring which can pose serious risks of tissue damage, resulting in the noted power limitations issue.

Various aspects of the present disclosure are directed to nano-patterned surface electrodes that can be implanted on a detrusor muscle to monitor a bladder volume status. In some implementations, the nano-patterned surface electrodes are composed of black silicon (BSi) of different density and dimensions coated with a conductive material. The nano-patterned surface electrodes exhibit a drastically reduced electrode impedance, which enables electrode miniaturization leading to a reduction in tissue inflammation and ensuing foreign body response, which enables this approach amenable for chronic bladder status monitoring.

In some implementations, a detection scheme for bladder volume monitoring is based on electrical impedance monitoring. For example, a sinusoidal wave (e.g., 1-100 mV, 50-100 kHz) is sent between two (2) nano-patterned electrodes that are implanted on the detrusor muscle. In operation, the impedance changes due to the bladder filling and emptying are detected by the implanted sensors and relayed through a transimpedance amplifier. According to various aspects of the present disclosure, a change in bladder impedance causes a change of the current passing through the transimpedance amplifier and leads to a change in an amplifier output voltage. The change in the amplifier output voltage may be utilized to provide bladder volume monitoring.

A large volume change takes place in humans from the "bladder empty" state (which holds just a few milliliters (ml) of urine) to the "bladder full" state (which holds approximately five-hundred milliliters (500 ml) of urine). This significant change in bladder states is easier to detect and less prone to errors due to drift and biofouling. By contrast, conventional solutions involve detection of a minimal change associated with an intra-vesicular pressure difference of approximately thirty-five centimeters of water (35 cm $H_2O$), which takes place from "bladder empty" to "bladder full" making pressure detection significantly more challenging.

Figure 1A:
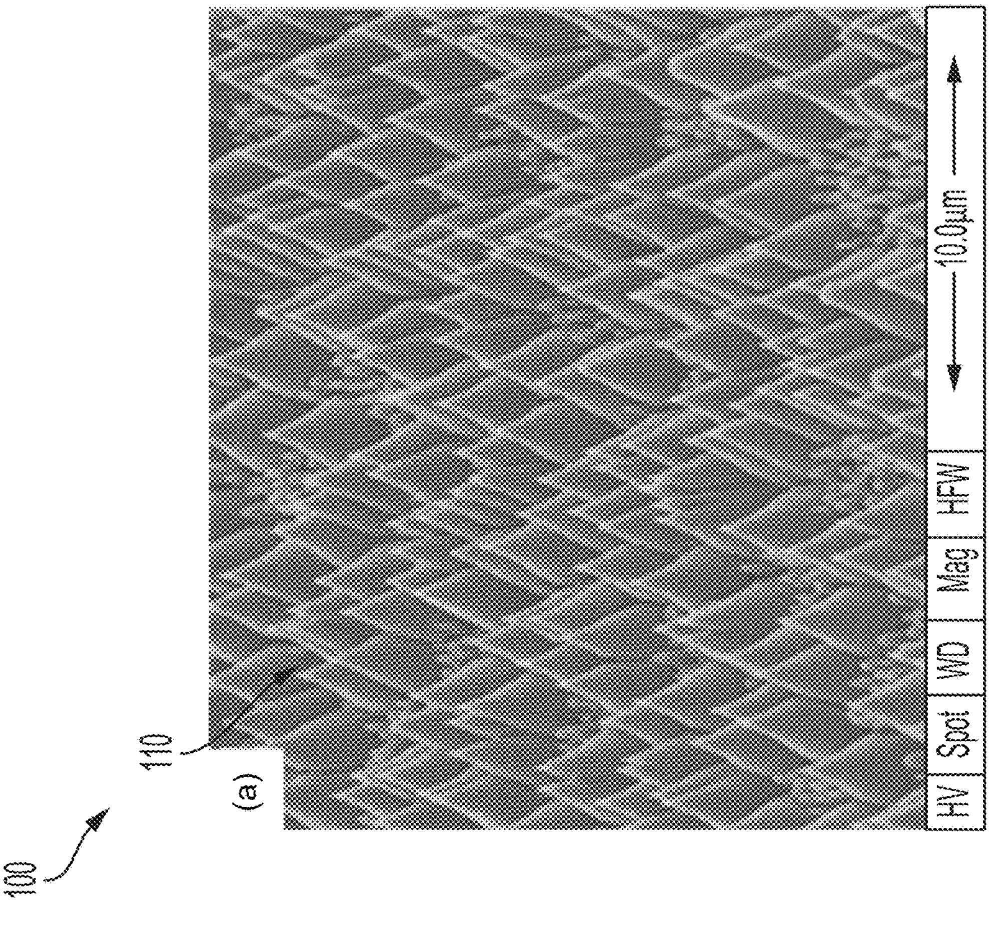
FIG. 1A is a scanning electron microscope (SEM) image of a dense conical black silicon (BSi) material, according to various aspects of the present disclosure.

FIG. 1A is a scanning electron microscope (SEM) image 100 of a dense conical black silicon (BSi) material, according to various aspects of the present disclosure. Biofouling is a crucial limitation that plagues surface electrodes from being utilized for successfully monitoring bladder volume. Biofouling tends to cause implant failure by dramatically increasing the sensor impedance. In particular, biofouling produces fibrotic tissue that is deposited on the sensor and operates as an electrical insulator that impairs the proper functioning of the implant. Various aspects of the present disclosure reduce biofouling by utilizing nano-patterning.

As shown in FIG. 1A, black silicon or BSi is composed of stochastically arranged, high aspect ratio, nano-pillars and micro-pillars that hinder protein deposition and cell adhesion, which reduces fibrotic tissue around a nano-patterned electrode implant. FIG. 1A illustrates conical BSi features 110 composed of nano and micro-features ranging from approximately five (5) micrometers (~5 μm)—from cone base and height to approximately ten (10) nanometers (~10 nm cone tip and nano-roughness).

FIG. 1B is a scanning electron microscope (SEM) image of dense conical black silicon (BSi) features 150, coated in a layer of high pressure sputtered conductive material, according to various aspects of the present disclosure. In some implementations, a high pressure sputtering of a conductive material (e.g., titanium/gold (Ti/Au), titanium/platinum (Ti/Pt), titanium/platinum iridium (Ti/PtIr), titanium/platinum/iridium (Ti/Pt/Ir), titanium/platinum/iridium oxide (Ti/Pt/IrOx), titanium/iridium (Ti/Ir), titanium/titanium nitride (Ti/TiN), titanium/platinum/titanium nitride (Ti/Pt/TiN), titanium/iridium oxide (Ti/IrOx)) over the conical BSi features 110 of FIG. 1A provides a conformal material coverage and high roughness to enable formation of the coated, dense conical BSi features 150 to enable formation of nanopatterned electrodes, according to various aspects of the present disclosure. As shown in FIG. 1B, the coated, dense conical BSi features 150 include a conformal, yet rough coating that is formed by depositing a layer of high-pressure Ti/Pt.

Figure 2:
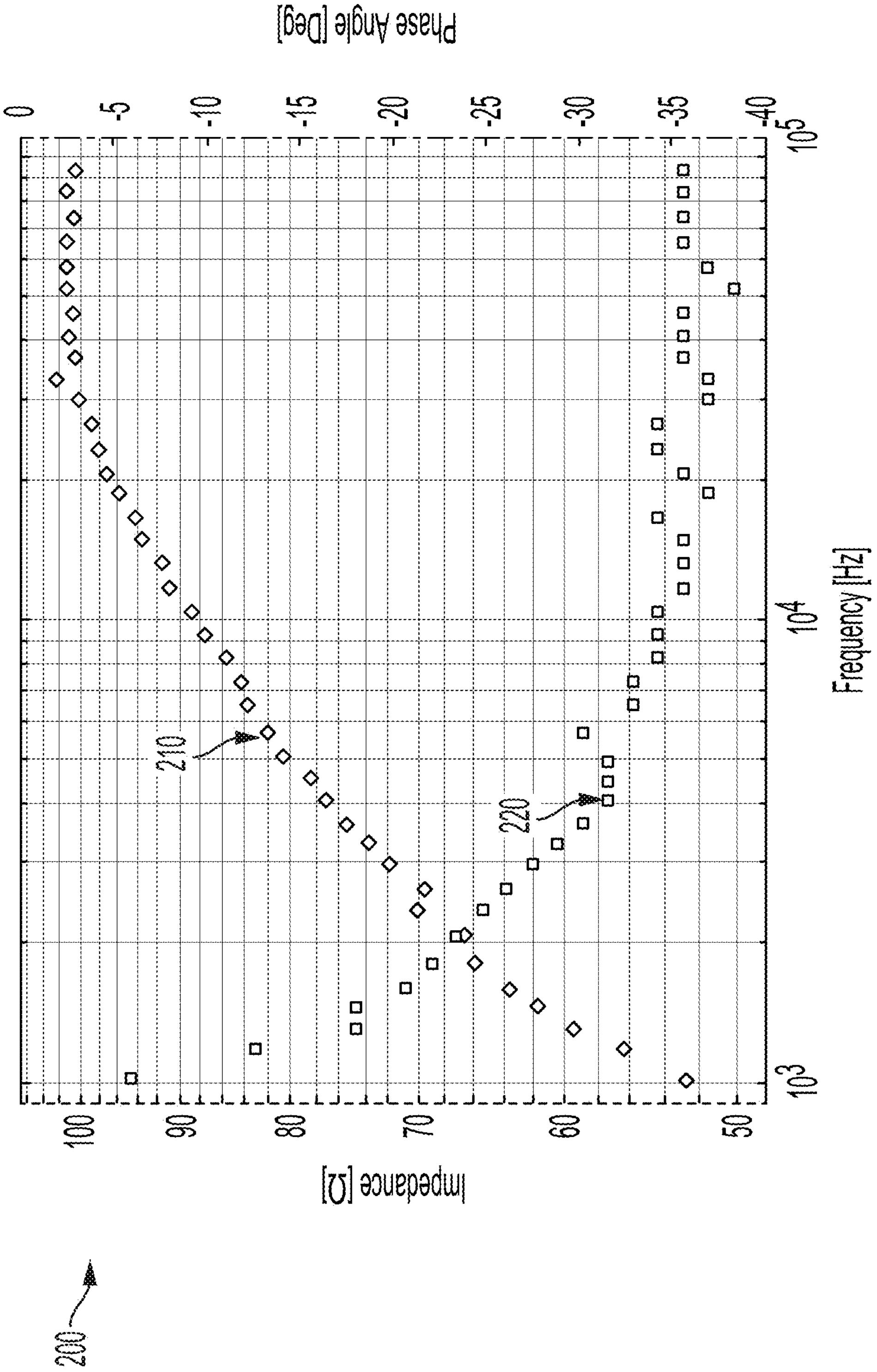
FIG. 2 is a graph illustrating an impedance as a function of frequency of dense, high pressure sputtered coated electrodes having a predetermined geometric area, according to various aspects of the present disclosure.

FIG. 2 is a graph 200, illustrating a representative example of the impedance of dense, high pressure sputtered coated electrodes as a function of frequency, according to various aspects of the present disclosure. The graph 200 illustrates that BSi drastically affects an electrode impedance ($Z_e$), which varies as a function of the electrode surface area ($Z_e \propto SA^{-1}$). In particular, BSi dramatically increases the electrode surface area (SA), which has a major effect on reducing the electrode impedance. In this example, the graph 200 illustrates an impedance signal 210 relative to a phase signal 220 of a Pt-coated electrode.

Various aspects of the present disclosure recognize the ability to produce an electrode with ultra-low impedance at baseline is important for minimizing the detrimental effects caused by some levels of biofouling. For instance, the graph 200 illustrates that conical BSi micro-cones coated in high pressure sputtered Ti/Pt show a reduction in $Z_e$ of approximately one (~1) order of magnitude compared to a smooth Pt electrode of the same size. For example, flat, Pt-coated electrodes with predetermined geometric areas (e.g., 2D of 1×1 $mm^2$) displayed an impedance of approximately three (3) kilOhm (~3 kΩ) at a predetermined frequency (e.g., 1 kHz) while Pt-coated BSi electrodes with the same geometric area displayed a significant decrease in impedance (e.g., ~100Ω at 1 kHz) of the noted one (1) order of magnitude, for example, as shown below in FIG. 7.

FIGS. 3A-3F illustrate components for performing bladder volume detection, according to various aspects of the present disclosure.

Figure 3B:
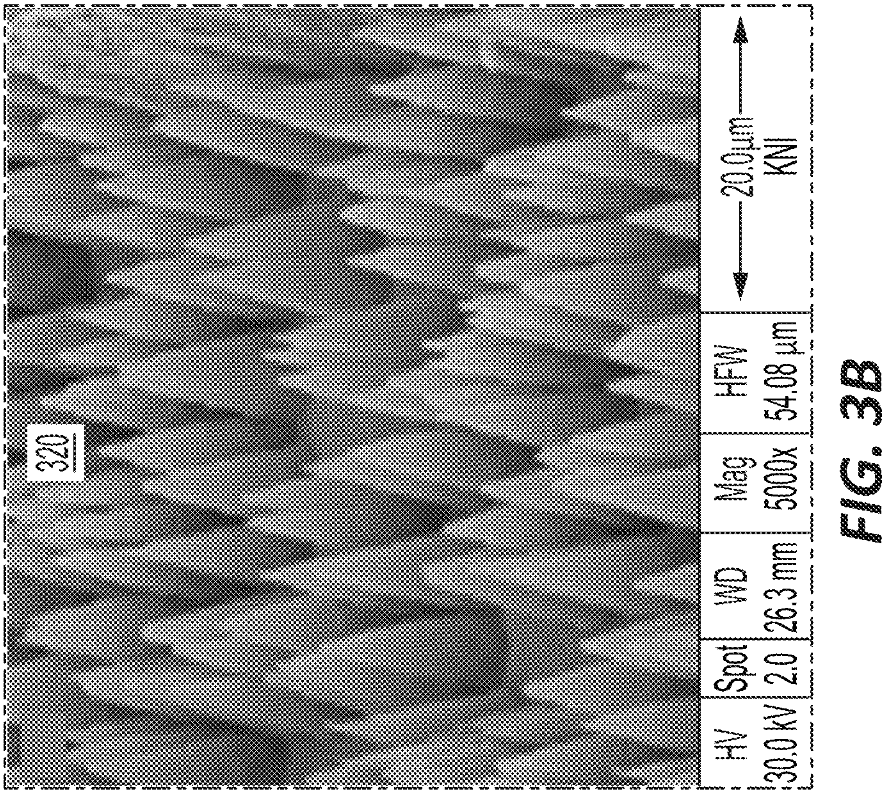
FIGS. 3A-3E illustrate components for performing bladder volume detection, according to various aspects of the present disclosure.
Figure 3A:
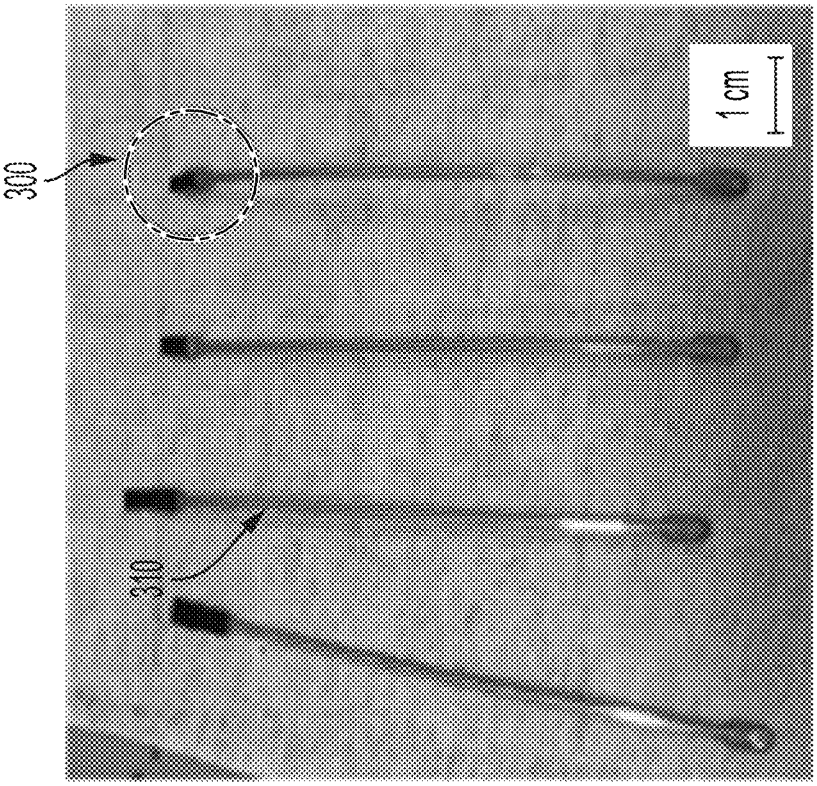

FIG. 3A is an optical image illustrating bladder volume sensors coupled to a communication cable, according to various aspects of the present disclosure. As shown in FIG. 3A, nano-patterned electrodes 300 can be packaged onto a flexible cable 310, such as a polyimide cable via thermo-mechanical bonding. For example, the mechanical bonding may be performed utilizing Indium bumps or by applying conductive paste between an electrode backside and a polyimide bonding pad. In some implementations, the nano-patterned electrodes 300 (e.g., bladder volume sensors) are further shown in FIG. 3B. FIG. 3B is a scanning electron microscope (SEM) image of a morphology of bladder volume sensors 320, composed of coated black silicon conical pillars, according to various aspects of the present disclosure.

Figure 3C:
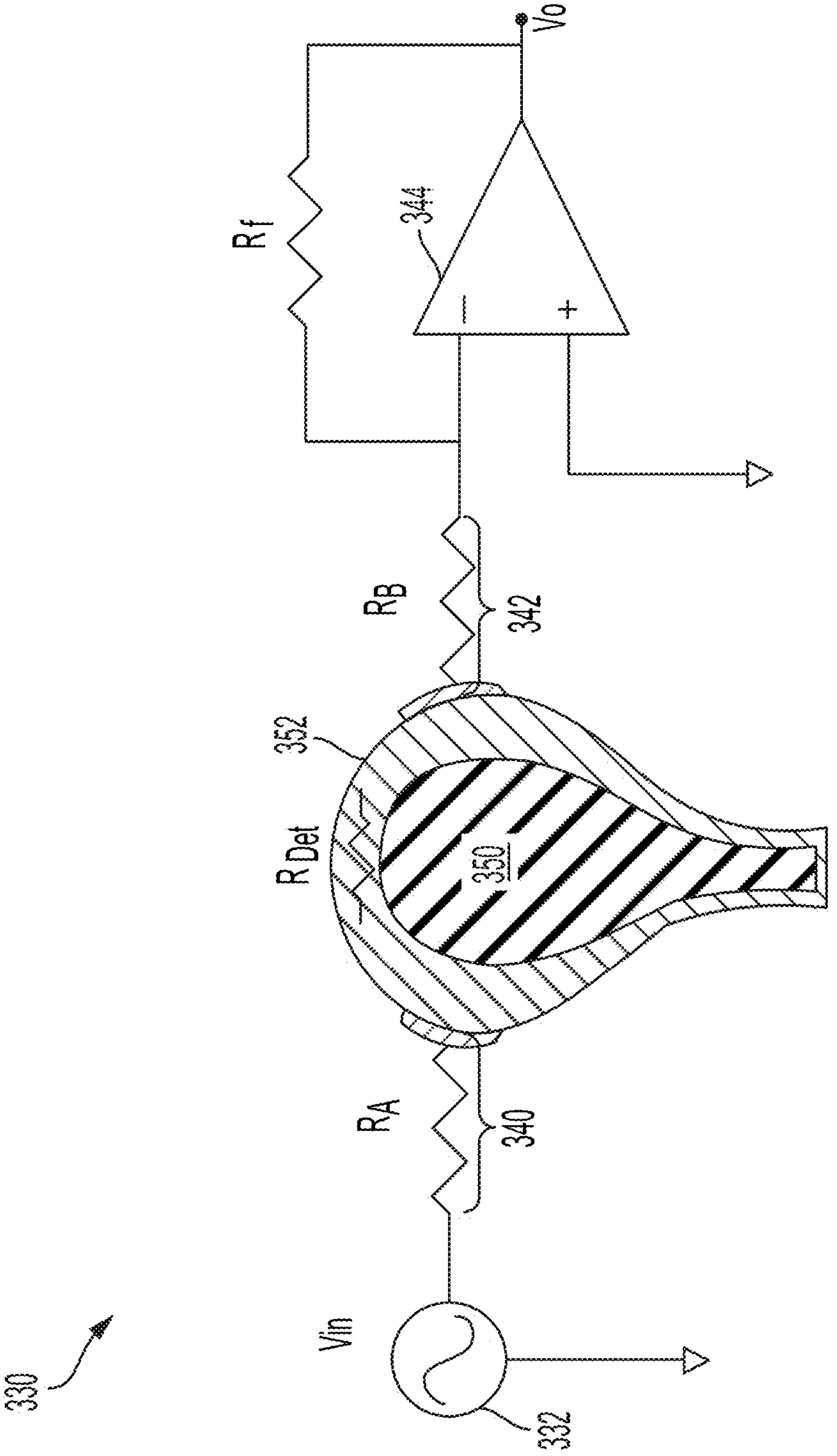

FIG. 3C illustrates a schematic representation of the bladder volume detecting circuit 330, according to various aspects of the present disclosure. In this example, a first nano-patterned electrode 340 and a second nano-patterned electrode 342 are implanted on a bladder 350. In various aspects of the present disclosure, an impedance detected between the first nano-patterned electrode 340 and the second nano-patterned electrode 342 is utilized for monitoring the bladder volume as the bladder 350 fills and empties.

As shown in FIG. 3C, the bladder volume detecting circuit 330 receives a sinusoidal input voltage Vin, which is coupled to the first nano-patterned electrode 340 having an associated resistance $R_A$. The first nano-patterned electrode 340 is coupled to the second nano-patterned electrode 342 through walls of the bladder 350. In this example, the bladder walls have an associated bladder wall impedance (e.g., a detrusor muscle resistance ($R_{Det}$)). In operation, the bladder volume detecting circuit 330 is coupled to an oscillator 332 that sends a sine wave with a given voltage and frequency (Vin signal). This Vin signal passes through the first nano-patterned electrode 340, the bladder wall 352, and the second nano-patterned electrode 342 before reaching the transimpedance amplifier 344. In this configuration, the first nano-patterned electrode 340, the bladder wall 352, and the second nano-patterned electrode 342 form a variable resistor (e.g., $R_A+R_{Det}+R_B$) that changes in value based on bladder volume. Because the gain (e.g., $V_0$/Vin) of the amplifier is determined by a ratio according to Equation (1), the gain will vary with bladder volume.

$$V_o = -\frac{R_f}{R_A + R_B + R_{Det}} V_{in} \quad (1)$$

Figure 3D:
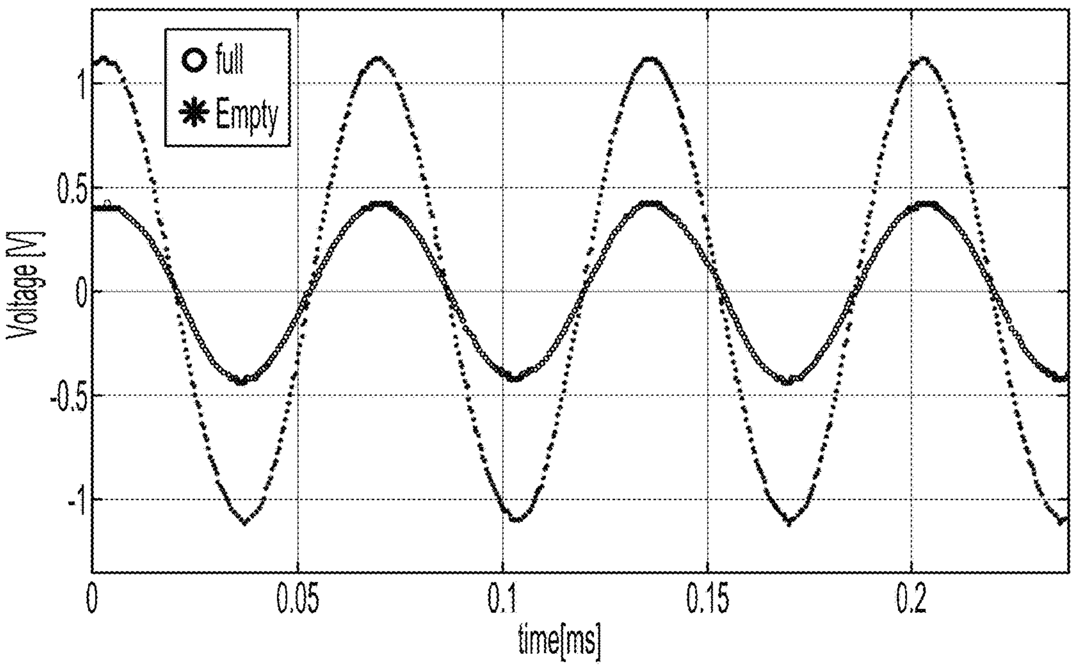
Figure 3E:
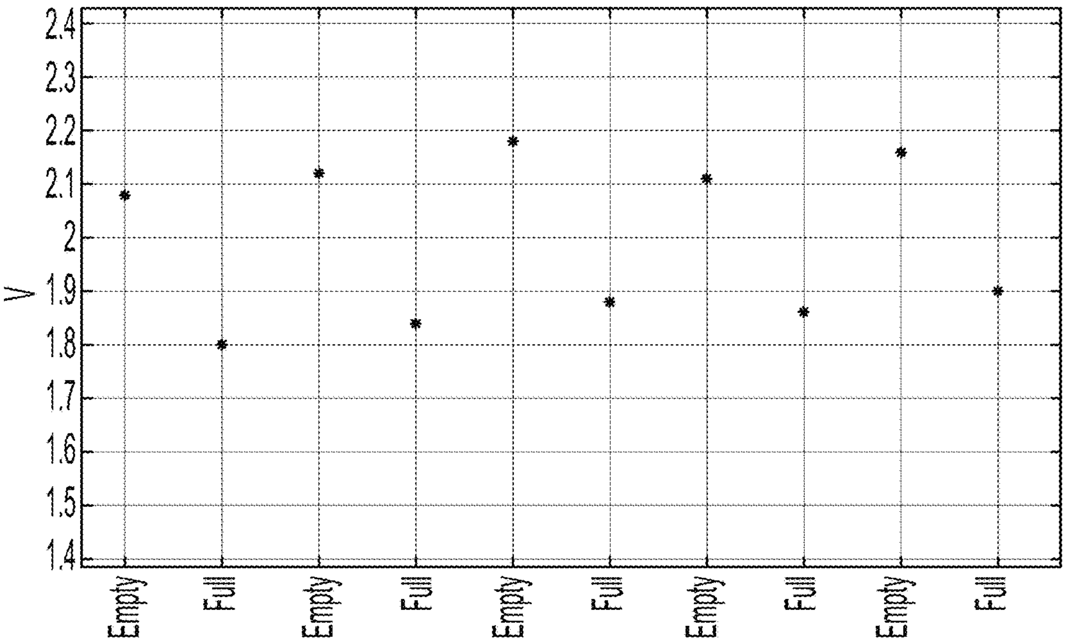

FIG. 3D illustrates a bladder volume graph 360 showing an in-vivo electrical recording of bladder volume changes during a micturition cycle, according to various aspects of the present disclosure. As shown in FIG. 3D, a sinusoidal wave of constant voltage Vin (e.g., ranging from 1-100 mV at 50 kHz) is sent between ground and the first nano-patterned electrode 340, which is not directly coupled to the transimpedance amplifier 344. The current that develops between the first nano-patterned electrode 340 and the second nano-patterned electrode 342 is modulated by the bladder wall impedance (e.g., $R_{Det}$) and is converted to the output voltage Vo by the transimpedance amplifier 344. The output voltage Vo of the transimpedance amplifier 344 changes based on the ratio of Rf, which remains constant, and the variable resistor formed by $R_A+R_{Det}+R_B$ according to bladder volume statues.

As shown in FIG. 3D, an amplified voltage evolves when the bladder is empty, which is shown as Vempty. By contrast, when the bladder volume increases, the bladder wall (e.g., detrusor) stretches, which increases the current path between the first nano-patterned electrode 340 and the second nano-patterned electrode 342, leading to an increase in impedance that is translated into a decrease in the output voltage $V_0$, as shown by the Vfull trace. During testing, a rat's bladder was used for this representative test and a volume change (e.g., of 0.4 ml) occurred between bladder empty and bladder full status, as shown by a graph 380 in FIG. 3E. Additionally, a corresponding voltage change (e.g., of ~300 mV) is recorded between bladder empty and bladder full status.

FIGS. 4A-4F illustrate a process for fabrication of black silicon nano-patterned electrodes coated in a conductive material, according to various aspects of the present disclosure.

Figures 4A, 4B, 4C, 4D, 4E, 4F:
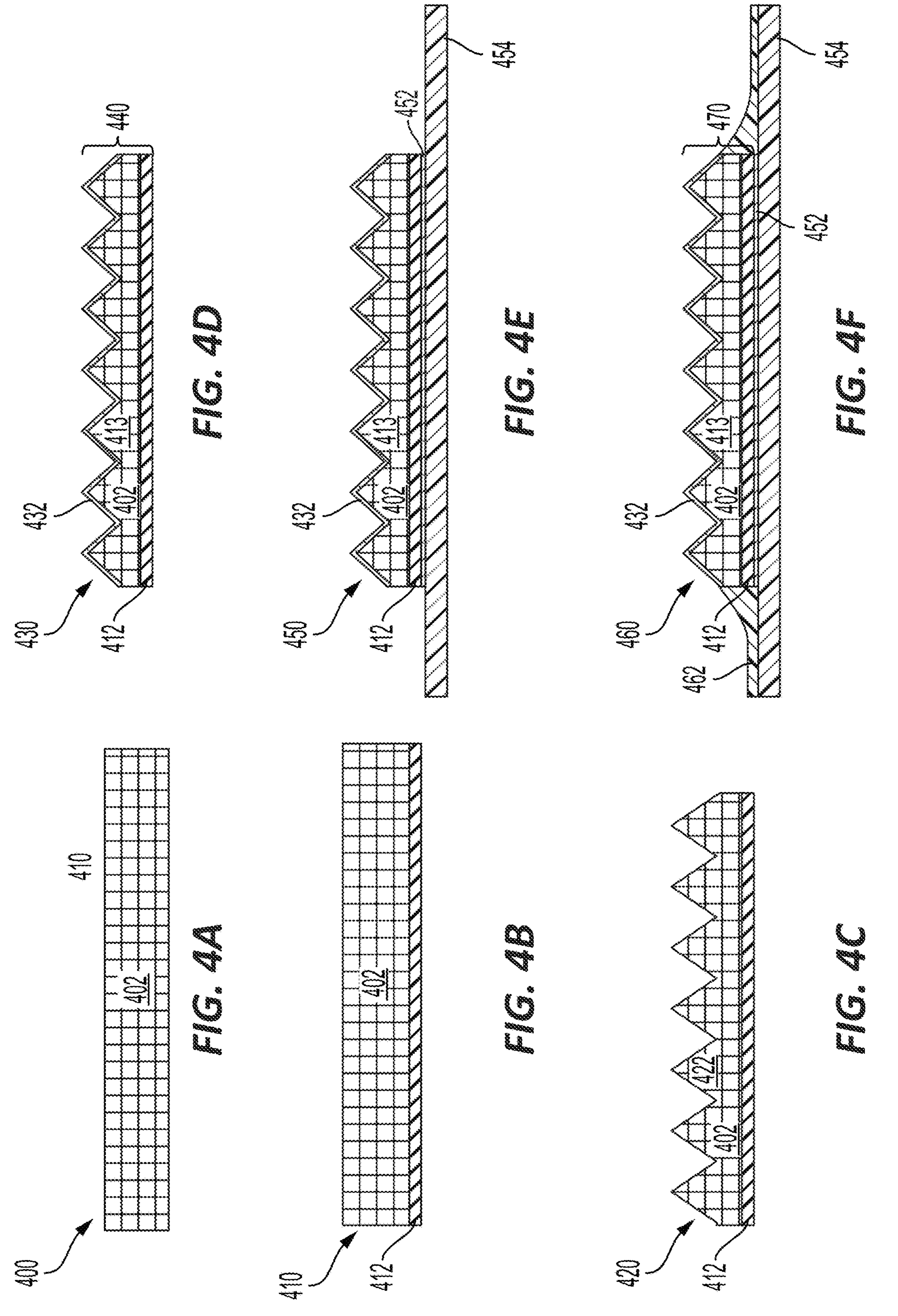
FIGS. 4A-4F illustrate a process for fabrication of black silicon nano-patterned electrodes coated in a conductive material, according to various aspects of the present disclosure.

As shown in FIG. 4A, at step 400, the fabrication process begins by thinning a wafer 402. For example, the wafer 402 may be a highly doped silicon (Si) wafer, having an N-type or P-type dopant at a predetermined dopant concentration (e.g., $>1\times10^{18}/cm^3$). Additionally, thinning of the wafer 402 may be performed via dry plasma etching, using an inductively coupled plasma (ICP) etcher. For example, sulfur hexafluoride ($SF_6$) can be used in an ICP etcher to thin a highly doped Si wafer down to a predetermined thickness (e.g., 100 μm).

As shown in FIG. 4B, at step 410, upon wafer thinning at step 400, the native oxide layer which is present on the wafer 402 is removed. For example, the native oxide layer on the wafer 402 is removed by dipping the wafer 402 in hydrofluoric acid for a few seconds. After oxide removal, a conductive material 412 (e.g., Ti/Au or Ti/Pt) is deposited on a backside of the wafer 402 using a sputter deposition or e-beam or thermal deposition, to provide a backside conductive layer (e.g., the conductive material 412).

As shown in FIG. 4C, at step 420, after metallization is completed at step 410, the wafer 402 is flipped and etched in a mixture of $SF_6/O_2$ gases at cryogenic temperatures (e.g., ranging from −110 °C to −160 °C). Either the ratio of $SF_6$ to $O_2$ or chamber pressure or chamber temperature can be used to determine the physical features of a BSi nano-patterned layer 422.

As shown in FIG. 4C, after formation of the BSi nano-patterned layer 422 at step 420, a native oxide present on a side of the wafer 402 having the BSi nano-patterned layer 422 is removed. For example, hydrofluoric acid is employed to remove the native oxide from the wafer 402.

As shown in FIG. 4D, at step 430, following oxide removal at step 420 of FIG. 4C, a conductive layer 432 (e.g., Ti/Au, Ti/Pt, Ti/PtIr, Ti/Pt/Ir, Ti/Pt/IrOx, Ti/Ir, Ti/TiN, Ti/Pt/TiN, Ti/IrOx) is sputter-deposited on a frontside of the wafer 402 having the BSi nano-patterned layer 422 (e.g., a frontside conductive layer). Once the conductive layer 432 is formed, the wafer 402 is diced so that individual sensors can be extracted to form a nanopatterned electrode 440 as a single chiplet.

As shown in FIG. 4E, at step 450, the nanopatterned electrode 440, which is formed as a single chiplet, is then bonded to a polyimide flexible cable 454 via either thermal bonding or by means of applying a bonding layer 452 (e.g., indium bumps, or conductive, biocompatible paste).

As shown in FIG. 4F, at step 460, a passivation layer 462 is formed by depositing a passivation material (e.g., Parylene C) that surrounds, but does not cover, the nanopatterned electrode 440. As shown in FIG. 4F, the passivation layer 462 is formed on sidewalls of the nanopatterned electrode 440 to encapsulate the nanopatterned electrode 440 and complete formation of a nanopatterned sensor 470. The passivation layer 462 also provides an encapsulation layer for the nanopatterned sensor 470, which may be utilized for bladder volume sensing.

Figure 5:
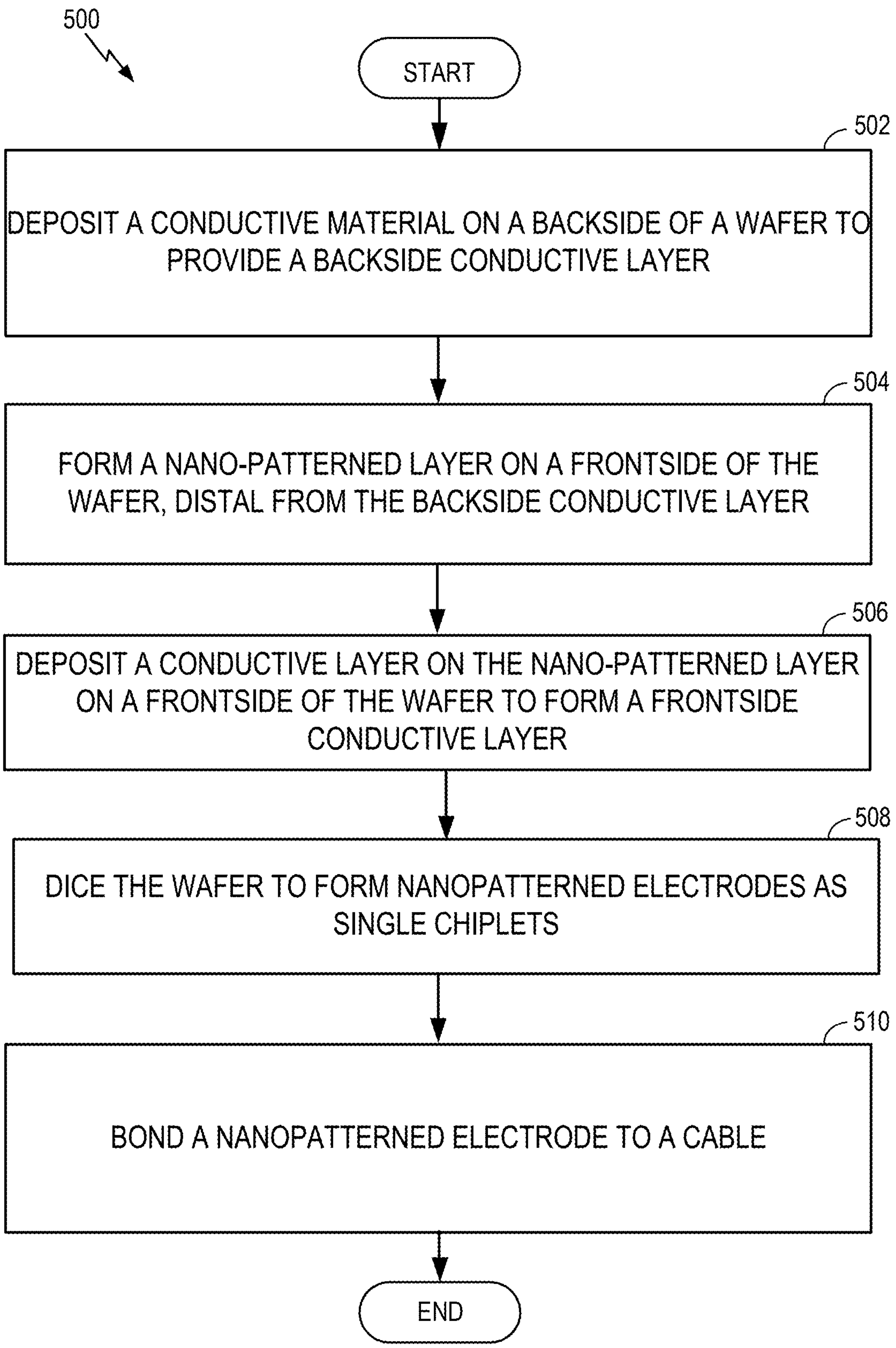
FIG. 5 is a flow chart illustrating a method for fabrication of black silicon nano-patterned electrodes coated in a conductive material, according to various aspects of the present disclosure.

FIG. 5 is a flow chart illustrating a method for fabrication of black silicon nano-patterned electrodes coated in a conductive material, according to various aspects of the present disclosure. A method 500 begins at block 502, in which a conductive material is deposited on a backside of a wafer to provide a backside conductive layer. For example, as shown in FIG. 4B, after oxide removal, a conductive material 412 (e.g., Ti/Au or Ti/Pt) is deposited on a backside of the wafer 402 using a sputter deposition or e-beam or thermal deposition, to provide a backside conductive layer (e.g., the conductive material 412).

At block 504, a nano-patterned layer is formed on a frontside of the wafer, distal from the backside conductive layer. For example, as shown in FIG. 4C, after metallization is completed at step 410, the wafer 402 is flipped and etched in a mixture of $SF_6/O_2$ gases at cryogenic temperatures (e.g., ranging from −110 °C to −160 °C). Either the ratio of $SF_6$ to $O_2$ or chamber pressure or chamber temperature can be used to determine the physical features of a BSi nano-patterned layer 422.

At block 506, a conductive layer is deposited on the nano-patterned layer on a frontside of the wafer to form a frontside conductive layer. For example, as shown in FIG. 4D, at step 430, following oxide removal at step 420 of FIG. 4C, a conductive layer 432 (e.g., Ti/Au, Ti/Pt, Ti/PtIr, Ti/Pt/Ir, Ti/Pt/IrOx, Ti/Ir, Ti/TiN, Ti/Pt/TiN, Ti/IrOx) is sputter-deposited on a frontside of the wafer 402 having the BSi nano-patterned layer 422 (e.g., a frontside conductive layer). Once the conductive layer 432 is formed, the wafer 402 is diced so that individual sensors can be extracted to form a nanopatterned electrode 440 as a single chiplet.

At block 508, the wafer is diced to from nanopatterned electrodes as single chip lets. For example, as shown in FIG. 4D, once the conductive layer 432 is formed, the wafer 402 is diced so that individual sensors can be extracted to form a nanopatterned electrode 440 as a single chiplet. At block 510, a nanopatterned electrode is bonded to a cable. For example, as shown in FIG. 4E, at step 450, the nanopatterned electrode 440, which is formed as a single chiplet, is then bonded to a polyimide flexible cable 454 via either thermal bonding or by means of applying a bonding layer 452 (e.g., indium bumps, or conductive, biocompatible paste).

Nanopatterned Micro-Electrodes for Neural Stimulation

Tissue stimulation began in the 1960s and has resulted in the commercialization of several life-saving therapies, especially in the cardiac environment. Neural stimulation also experienced tremendous success, leading to revolutionizing treatments such as deep brain stimulation (DBS) for Parkinson's disease, spinal cord stimulation for chronic pain reduction, sacral nerve stimulation to induce bladder and bowel voiding in paralyzed people, and more. In recent years, the neurotech space has seen dramatic advancements targeted toward the development of high-bandwidth, bi-directional brain machine interfaces (BMI) and brain computer interfaces (BCI). Today, a great amount of effort is devoted to neural sensing, while stimulation is traditionally labeled as a mature and known technique. Unfortunately, the desire for spatially selective, stable and safe stimulation involves technology that is not yet fully developed.

In practice, establishing communication with neural populations via action potential generation is important for building functionally targeted BMI. In essence, neural stimulation involves delivering a threshold charge density (Qth) in the vicinity of the target cell population to trigger action potentials (AP). One commonly employed method for delivering charge to excitable cells (e.g., neurons) is current controlled stimulation (CCS). CCS has the advantage of ensuring that a given amount of charge is delivered to the tissue at the expense of potentially developing unsafe voltages for both the stimulating electrode and the target tissue. The maximum allowed voltage is material dependent and specified to fall within a "water window" for avoiding electrolysis, which damages neural tissue and corrodes the stimulation electrode. For example, platinum (Pt), which is a commonly employed electrode material, has a water window (e.g., ranging from −0.6-0.8V). Other commonly used materials such as TiN, IrOx offer a broader water window but are either less conductive (TiN ~$1\times10^5$-$1\times10e^6$ S/cm, VS Pt ~$1\times10^7$ S/cm) or more complex and expensive to prepare (AIROF).

Conventional neural stimulation techniques exhibit various deficiencies, including: (1) poor resolution, (2) poor electric field confinement, and (3) short electrode longevity. For example, cortical stimulation such as deep brain stimulation (DBS) uses large electrodes (e.g., on the order of ~1 mm in diameter) and targets groups of neurons that are organized three-dimensionally. Therefore, DBS is not selective to any specific neuronal compartment (e.g., the soma, dendritic arbor, or axon). When somas are activated by direct electrical stimulation, a variety of post-synaptic responses may be elicited, resulting in possible signal inhibition or non-directional AP spreading.

A second type of stimulation that does not rely on penetrating probes employs surface or cuff electrodes and is often used for epidural or peripheral stimulation. For example, cuff electrodes, which are commonly used for peripheral nerve stimulation, primarily target axons that run parallel to the electrode array, which improves AP propagation reliability. Unfortunately, as a result of the large distance between the stimulating electrodes and the target axons, the stimulating current needs to be increased, which leads to broad, non-selective cell activation.

Aside from the intrinsic architecture of the brain, one of the core issues affecting stimulation resolution lies in the inability to scale down electrodes in size. For effective stimulation to take place, which is defined as the ability to elicit AP propagation in the target neuronal population, a certain amount of charge (e.g., threshold charge ($Q_{Th}$)) is required. State of the art, commercially available electrodes deliver $Q_{Th}$ via flat, metallic surfaces coated in Pt, Au, Ir, IrOx. A limited charge delivery capability (CDC) and relatively poor conductivity of thin films strongly limits the minimum dimensions of such electrodes, thereby capping the maximum available spatial resolution.

In practice, the ability to deliver charge strongly depends on two factors: (1) the electrode charge injection limit (CIL), which indicates how much charge an electrode can handle before damage occurs; this parameter is material dependent with values ranging from (~150 μC/cm$^2$) for evaporated, low roughness Pt to ~3000 μC/cm$^2$ for activated IrOx (AIROF), and (2) Electrode impedance ($Z_e$). Electrode impedance $Z_e$ plays a key role in charge transfer and voltage evolution at the tissue-electrode interface during stimulation, which is specified to lie within the electrode material's water window to avoid faradaic currents caused by RedOX reactions at the interface. Additionally, both CIL and electrode impedance $Z_e$ depend on the available electrode surface area ($Z_e \propto SA^{-1}$) which, for 2D flat surfaces, is limited to modulation via increasing electrode dimensions, making flat electrodes inherently incompatible with electrode miniaturization. Because miniaturization is crucial for increasing spatial resolution, a different approach is desired.

Peripheral nerve, deep brain, spinal cord and responsive neurostimulation are well established therapies that have proven to be safe and effective. The nature of such treatments does not require a high level of spatial selectivity and activated areas often cover several mm$^2$. More recently, the drive to build neural interfaces capable of restoring sensation with a high degree of spatial selectivity has led to the development of microelectrode arrays where each electrode can activate cells in its vicinity, without activating cells located nearby other electrodes. This type of highly selective stimulation is challenging on both electrode miniaturization and inter-electrode spatial arrangement grounds.

Currently, the most commonly used stimulation approach is monopolar which involves an active microelectrode that swings up and down—effectively functioning as both cathode and anode—with respect to a fixed reference electrode. The reference electrode is often located far away (>>100 μm) from the active electrode which produces a large volume of tissue activation (VTA) preventing highly specific neuronal activation. Less commonly employed stimulation routes consist of bipolar and, to some extent, tripolar stimulation where all the electrodes involved in stimulation are active and are in close proximity to each other. A major drawback affecting bipolar stimulation lies in the higher impedances carried by the stimulating electrodes due to their smaller dimensions, implying that for a given constant current a larger interfacial voltage will be generated compared to monopolar stimulation, possibly causing tissue and electrode damage. Conversely, the major advantage of bipolar stimulation is associated with smaller VTA, which can drastically improve stimulation focality.

The insertion of a device into the body will lead to a certain amount of device degradation regardless of the device composition or form factor. Controlling this degradation process is crucial for chronic implants. Two processes result in device degradation: (1) abiotic and (2) biotic. The former causes device corrosion, insulation failure, and material delamination, ultimately leading to either short or open circuit problems. Such abiotic damage results from redox reactions at the electrode-tissue interface which causes local pH and temperature changes leading to electrode etching. The latter ensues from the disruption of the natural biological environment following mechanical insertion of the device. The physical damage caused by the device leads to disruption of the blood brain barrier (or blood-spinal cord barrier (SCBB)), loss of perfusion, neuronal degeneration, and secondary metabolic injury which trigger the body's inflammatory response. Long-term inflammation activates a chronic foreign body response which eventually leads to biofouling and possible device encapsulation which, in the case of stimulating electrodes, dramatically increases electrode impedance and can impair the stability of the device over time.

Spatially selective neural stimulation is necessary to re-establish targeted sensation in paralyzed patients. Current electrodes such as flat platinum (Pt) electrodes suffer from numerous critical drawbacks, including physical degradation and biofouling. As a result of these drawbacks, an electrode size utilized for spatially selective neural stimulation cannot be scaled down to desired dimensions (e.g., <50×50 μm$^2$). Moreover, the return electrode is usually placed far away (e.g., >100 μm) from the stimulating electrode. These limitations result in widespread cell activation, which prevents high-resolution and spatially selective stimulation.

Various aspects of the present disclosure circumvent these limitations by means of nanopatterning the stimulating and reference electrodes, resulting in a dramatic decrease of the electrode impedance ($Z_e$) and an increase in charge density capability (CDC) due to the larger available surface area. In some implementations, nanopatterning is based on black silicon (BSi), which is a surface modification of silicon that exhibits high levels of surface roughness as a result of its extremely dense, high-aspect ratio (AR) nano-strands.

Various aspects of the present disclosure disclose conical BSi which features a combination of micrometer sized features (e.g., cone base ~5 μm, height ~10 μm) and nanometer sized features (e.g., <100 nm) that form over the conical surface as a result of the inherent porosity of BSi. In some implementations, the BSi electrodes are coated with a mixture of low and high pressure sputtered conductive material (HPC), such as platinum (Pt) to ensure a conformal, yet dense interfacial film that contributes to the decrease in $Z_e$.

Aside from the physical features, the disclosure electrodes take advantage of the native functional organization of the spinal cord by utilizing custom-made nanopatterned electrodes, which improve signal-to-noise ratio, charge injection, and electrode stability over time. The white matter in the spinal cord communicates with the brain in one-dimension and is characterized by somatotopy in which representations of motor and sensory activity of the body are discretely and spatially organized in axon bundles. The collection of these axon bundles, which occupies ~1 $cm^2$, holds all the motor and sensory information that is being exchanged between the body and the brain. As a result of this intrinsic map and compactness of information within the spinal cord, stimulation of target areas becomes simpler and fewer than 500 electrodes of ~30×30 $\mu m^2$ and would be necessary to restore sensation to over 90% of the body, making spinal cord machine interfaces the best candidate for developing neural interfaces capable of restoring both sensation and motor control in paralyzed people.

Various aspects of the present disclosure provide methods for fabricating conductive material-coated, black silicon (BSi)-based nanopatterned electrodes. For example, the BSi features range from dense grass to sparse conical BSi features. The exponentially larger surface area of these electrodes beneficially reduces the electrode impedance $Z_e$ and increases CDC, thereby enabling electrode miniaturization. Miniaturization of electrodes that maintain low $Z_e$ (e.g., <50 kΩ@1 kHz) enables high resolution, high spatial selectivity (e.g., <100 μm spread) stimulation. For example, sputtering deposition of Pt at high pressure (HPPt) (e.g., >20 mtorr) results in a highly conformal, low stress, rough film which leads to a higher degree of film porosity. Such high porosity effectively expands the total available surface area (SA) and leads to a drastic reduction in $Z_e$. The scalability of this platform, combined with its compatibility with silicon nanofabrication techniques, provides a clear path towards simultaneous, high-fidelity interfacing with thousands of individual neurons per $mm^2$.

FIGS. 6A-6D are scanning electron microscope (SEM) images of black silicon (BSi) material features, according to various aspects of the present disclosure. FIGS. 6A-6D further illustrate various examples of nanopatterning, according to various aspects of the present disclosure.

Figure 6B:
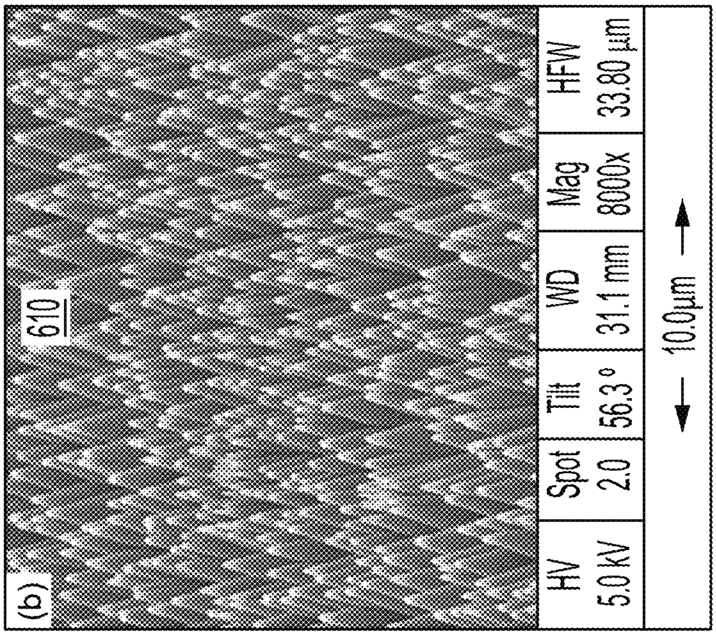
FIGS. 6A-6D are scanning electron microscope (SEM) images of black silicon (BSi) material features and further illustrate various examples of nanopatterning, according to various aspects of the present disclosure.
Figure 6A:
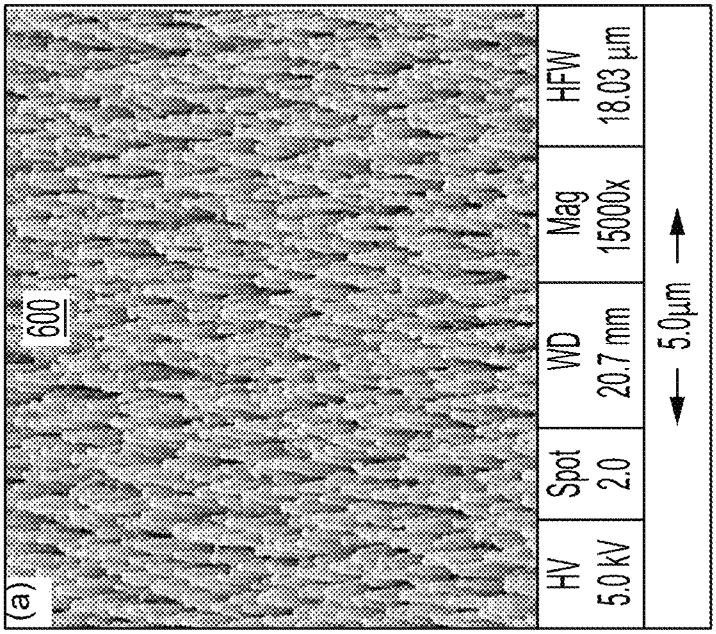
Figure 6C:
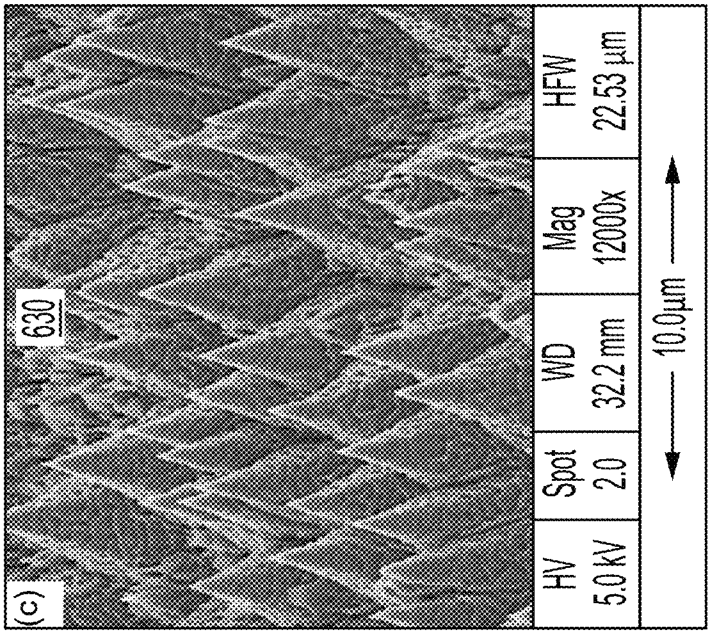
Figure 6D:
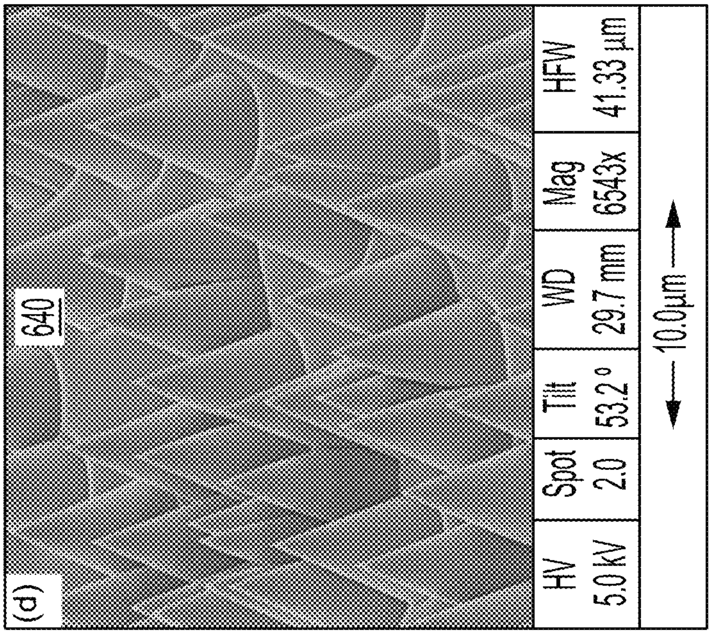

FIG. 6A is an SEM image of grass-type dense BSi features 600, according to various aspects of the present disclosure. FIG. 6B is an SEM image of high aspect ratio, dense BSi features 610, according to various aspects of the present disclosure. FIG. 6C is an SEM image of conical BSi features 630 with high surface roughness, according to various aspects of the present disclosure. FIG. 6D is an SEM image of sparse, conical BSi features 640, according to various aspects of the present disclosure.

FIGS. 6A-6D illustrate the ability to tune a BSi feature shape from the grass-type dense BSi features 600 of FIG. 6A to the sparse, conical BSi features 640 of FIG. 6D. The density and dimensions of the conical BSi features 640 can also be tuned from a high-density regime, such as the dense BSi features 610 shown in FIG. 6B, to a sparse regime, such as the sparse, conical BSi features 640 shown in FIG. 6D. Additionally, a nano-roughness that can be introduced in the BSi features that is evident by comparing the morphological difference between FIGS. 6C and 6D, with FIG. 6C displaying a nano-roughness that covers the entire surface of the micro-cones of the conical BSi features 630, leading to an exponential increase in their effective surface area (SA).

Various aspects of the present disclosure provide concentric, BSi-based, high surface roughness Pt-electrodes that deliver a low electrode impedance $Z_e$ and a high charge density capability (CDC). In some implementations, the disclosed micro-electrodes dramatically increase stimulation resolution to pave the way for high spatial selectivity neural stimulation. The disclosed conical BSi features shown in FIGS. 6B-6D combine micro and nano-sized features. For example, a cone base includes a predetermined base range (e.g., from ~1-5 μm), and a predetermined cone height range (e.g., from ~10-20 μm) Additionally, the cone surface displays nano-roughness with an average height (e.g., ~100 nm), as shown in FIG. 6C.

According to various aspects of the present disclosure, a three-dimensional electrode array is composed of nanopatterned electrodes, for example, as shown in FIG. 6A-6D. In some implementations, each nanopatterned electrode is composed of black silicon (BSi) features having different shapes ranging from dense grass to sparse cones. The different BSi features can take different aspect ratios (e.g., ranging from 2:1 to 100:1), as shown in FIG. 6A-6D.

Figure 7B:
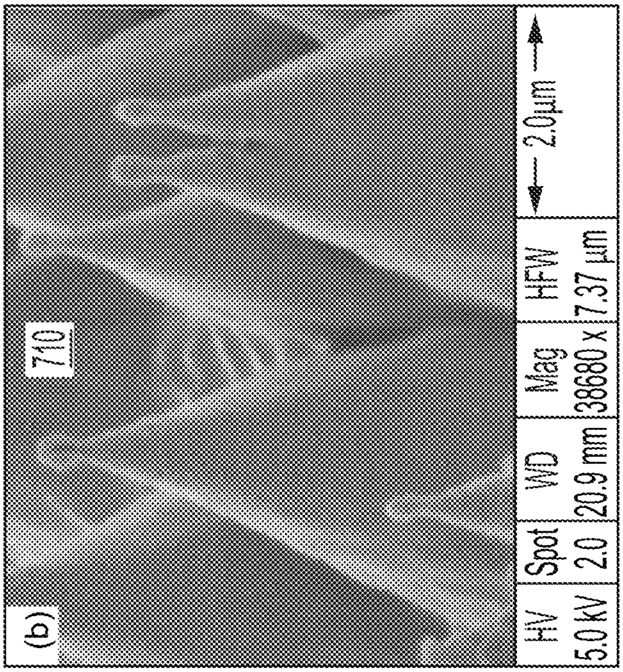
FIGS. 7A-7D dense, high-pressure sputtered black silicon (BSi) electrodes having high conductivity micro-cones and associated conductivity results, according to various aspects of the present disclosure.
Figure 7A:
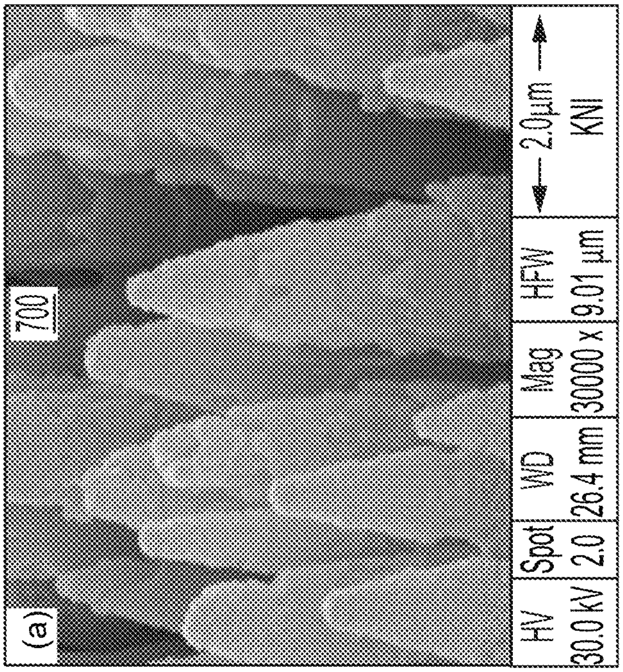

FIGS. 7A-7D illustrate dense, high-pressure sputtered black silicon (BSi) electrodes having high conductivity micro-cones and associated conductivity results, according to various aspects of the present disclosure. FIG. 7A is a scanning electron microscope (SEM) image of dense, high-pressure sputtered BSi electrodes 700. FIG. 7B is an SEM image of sparse, conical high-pressure sputtered BSi electrodes 710. According to various aspects of the present disclosure, a high pressure (HP) conductive material (e.g., platinum (Pt)) sputtering provides high-conductivity micro-cones, for example, as shown in FIGS. 7A and 7B.

Figure 7D:
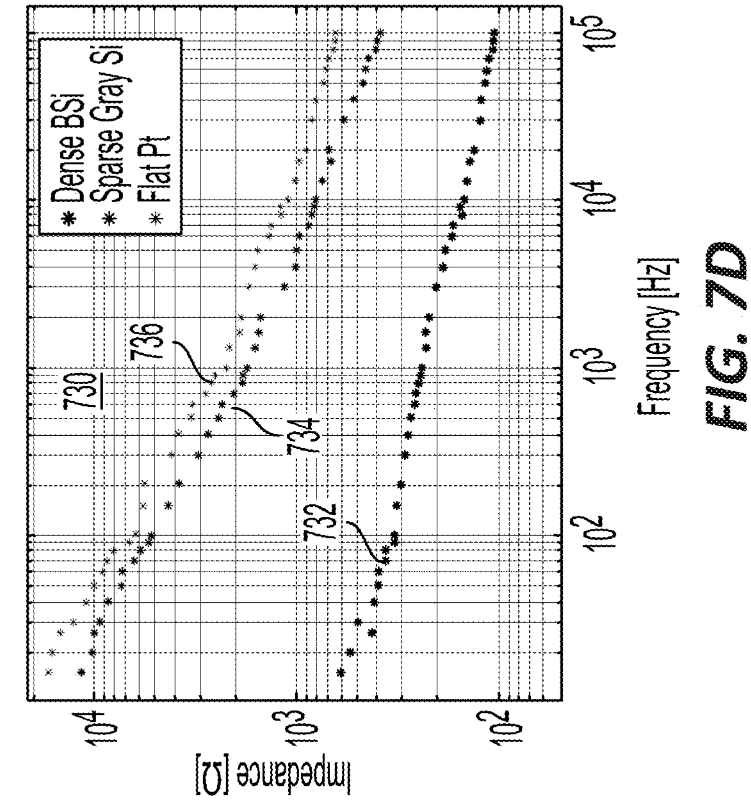
Figure 7C:
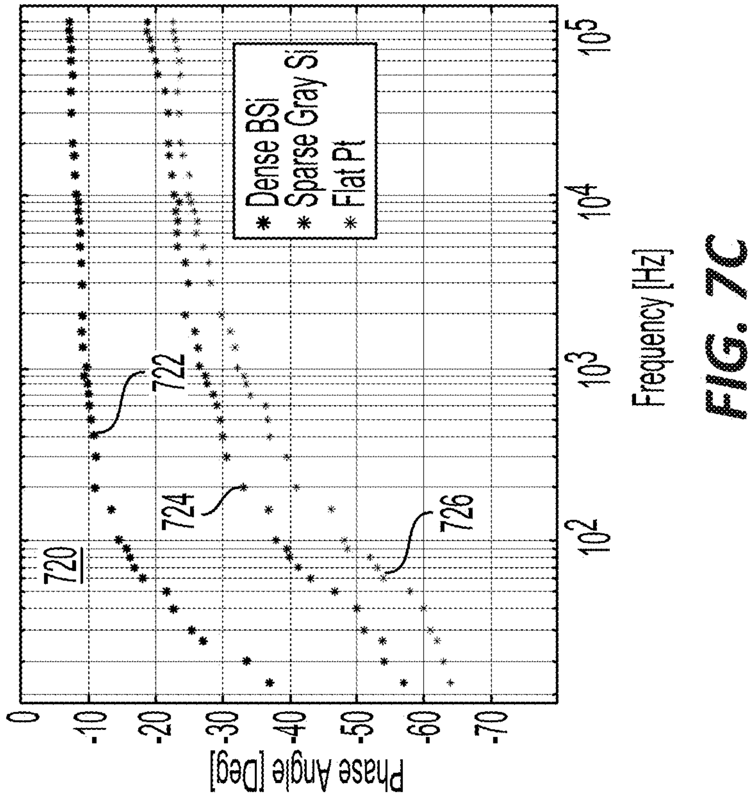

FIG. 7C is a graph 720 illustrating a phase angle as a function of a frequency of a dense, high-pressure sputtered (HPS) BSi electrode 722, a sparse, HPS gray silicon (GSi) electrode 724, and a flat electrode 726, according to various aspects of the present disclosure. FIG. 7D is a graph 730 illustrating an impedance as a function of frequency of a dense, HPS BSi electrode 732, a sparse, HPS GSi electrode 734, and a flat electrode 736, according to various aspects of the present disclosure.

FIGS. 7C and 7D illustrate tests results on the conical HPPt-BSi micro-cones, which show a significant reduction in electrode impedance $Z_e$ (e.g., ~1 order of magnitude) compared to the smooth Pt electrode (e.g., the flat electrode 736) of the same size (FIG. 7D). The test results were prepared based on predetermined sized (e.g., 1×1 $mm^2$) electrodes composed of (1) a flat electrode, (2) a sparse HPS-BSi (FIG. 7B), and (3) a dense HPS-BSi electrode (FIG. 7A) and performed using electrochemical impedance spectroscopy (EIS) measurements. FIG. 7D illustrates a substantial reduction in the electrode impedance $Z_e$ between the flat electrode 736 (e.g., ~2kΩ) and the dense HPS BSi electrode 732 (e.g., ~230Ω at 1 kHz) (FIGS. 7C-7D). FIG. 7D further illustrates a dramatic change in the electrode impedance $Z_e$ relative to the impedance (e.g., ~1.6 kΩ) of the sparse HPS GSi electrode 734, which confirms the ability of dense BSi to contribute to a significant decrease in the electrode impedance $Z_e$.

As recognized by various aspects of the present disclosure, a certain amount of threshold charge density ($Q_{th}$) is specified to transfer from the stimulating electrode to a target cell to trigger an action potential (AP) for neural stimulation. As described, the threshold charge density $Q_{th}$ is defined as charge over geometric area (2D) of the stimulating electrode and exhibits a predetermined range (e.g., ~200-2000 μC/$cm^2$) for neural tissue depending on the stimulation location and distance to the target cells. On the other hand, a charge density capacity (CDC) depends on a total surface area (3D) of the stimulating electrode. Therefore, increasing a three-dimensional area of an electrode enables attainment of a desired charge density $Q_{th}$ without violating the material's charge injection limit (CIL), which is determined by the effective three-dimensional surface area of the electrode.

Additionally, the charge density $Q_{th}$ is much larger than the CIL for the flat electrodes 726/736. As a result, a representative microelectrode having predetermined dimensions (e.g., 30×30 $\mu m^2$) could be severely damaged during stimulation. Nevertheless, a BSi-based, Pt-coated electrode displays an increase in total surface area (SA) of at least one (1) order of magnitude, while maintaining the same geometric area. Therefore, the BSi-based, Pt-coated electrode can effectively transfer a threshold charge density Qth (e.g., ~200-1000 μC/$cm^2$) and one hundred (100) micro-coulombs (μC) over its entire surface area, without exceeding the CIL for Pt, ensuring electrode safety.

As an example, assume a 2D flat electrode with specified dimensions (e.g., 30×30 $\mu m^2$) and a specified Qth (e.g., 1000 μC/$cm^2$). In this example, a constant current charge is calculated by integrating the current pulse by a predetermined amount of time, which represents the pulse duration that commonly varies (e.g., between 200-400 us). The necessary current for reach $Q_{th}$ is calculated to be 22 uA for a 400 us pulse duration. This is equivalent to 1000 uC/cm^2 which is ~5 times higher than the CIL for Pt (~200 uC/cm^2) leading to electrode damage. On the other hand, increasing the electrode surface area by 1 order of magnitude while maintaining the same 2D geometric area (e.g., 30×30 $\mu m^2$), leads to a charge over the effective 3D surface area of 100 uC/$cm^2$, which is within the limits posed by the CIL for Pt, ensuring electrode safety.

Similarly, the electrode impedance $Z_e$ is significantly affected by the total electrode SA (e.g., $\propto SA^{-1}$). Increasing the electrode effective SA maintains a relatively small geometric area (e.g., ranging from 400-900 $\mu m^2$), which is essential to improve stimulation resolution, without increasing electrode impedance $Z_e$. Reducing the electrode impedance $Z_e$ is important for effectively increasing a usable current range. Additionally, minimizing the voltage evolution during stimulation enhances electrode robustness. Because the electrode impedance $Z_e$ inevitably increases over time, mostly due to biofouling, minimizing the electrode impedance in its pristine state is important for reducing the possibility of evolving voltages exceeding the water window after prolonged use. In addition to lower impedance, the mechanical stability of HPC-BSi electrodes was confirmed by performing peeling tests.

In addition to charge density capacity (CDC) and the electrode impedance $Z_e$, a third parameter that is important to ensuring long term electrode stability is related to the electrode's ability to reduce biofouling. Protein adsorption, gliosis, and organic encapsulation are natural consequences of placing a foreign object in the body, which results in electrode passivation and often eventually lead to a device malfunction. Biofouling begins via serum protein adsorption and consequent cell attachment, which is inhibited to a large extent on nanopatterned surfaces. The high aspect ratio nanofeatures of BSi leads to a drastic increase in cell membrane stress upon attachment, resulting in membrane rupture and cell death which gives BSi its anti-microbial and bactericidal properties. Mammalian cells are too large for death to occur; however, BSi severely hinders their attachment, resulting in a significant decrease in biofouling and making the disclosed electrodes more amenable for chronic stimulation.

Figure 8B:
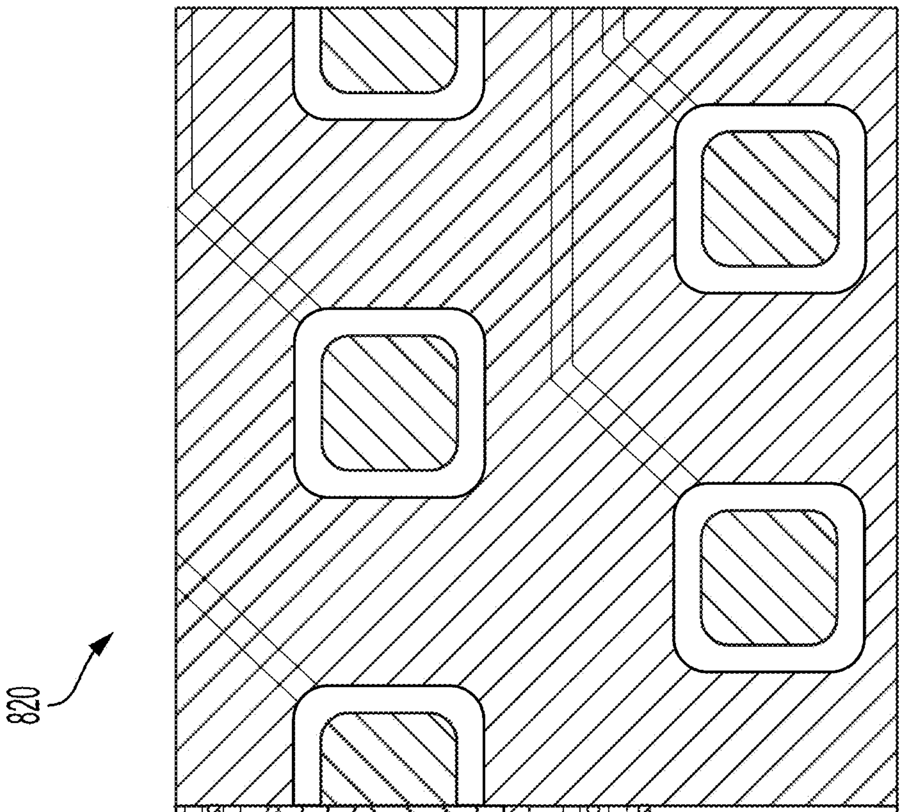
FIGS. 8A and 8B are schematic representations of a concentric-type electrode configuration (CC) and a ground sheet electrode configuration (GS), according to various aspects of the present disclosure.
Figure 8A:
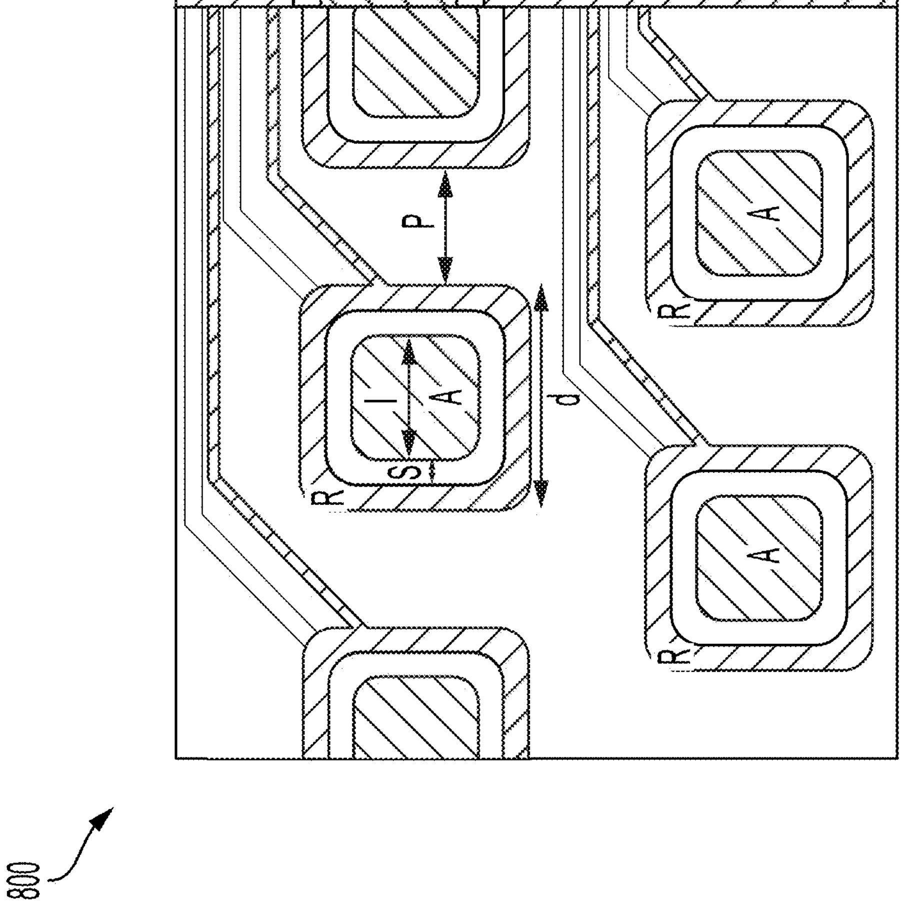

FIGS. 8A and 8B are schematic representations of a concentric-type electrode configuration (CC) and a ground sheet electrode configuration (GS), according to various aspects of the present disclosure. FIGS. 8A and 8B illustrate electrode configurations that solve a final factor that is key to creating a high resolution, spatially selective neural stimulator involving significantly improving electric field confinement. Focality, which is the ability to concentrate the electric pulse to a small volume tissue activation (VTA), is important for achieving high activation resolution. Additionally, a proximity of the source and sink electrodes is shown to shape the electrical response of the target tissue.

Using either a CC 800 of FIG. 8A or a GS 820 of FIG. 8B yields better focality and higher resolution compared to the standard electrode configuration where a return electrode is placed far away from an active electrode A. As shown in FIG. 8A, in the CC 800, an interplay between an electrode unit cell size (electrode length (l)+a reference electrode R length (d)+an active-to-reference electrode spacing(s)) and inter-electrode pitch (p) are important factors in determining resolution. Additionally, a spacing (s) between the active electrodes A and reference electrodes R is important for determining focality.

In this example shown in FIG. 8A, the active-to-reference electrode spacing s modulates the electric field between the active electrodes A and the reference electrodes R, which ultimately determines the successful initiation of an action potential. Additionally, controlling the impedance that develops between the active electrodes A and the reference electrodes R (ZAR) during stimulation is paramount for confining the stimulating electric field. ZAR is usually controlled by varying the spacing s; for instance, increasing the spacing s also decreases a spatial resolution.

Various aspects of the present disclosure propose a method that provides modulation of ZAR without increasing the electrode footprint. In some implementations, this method involves creating a dam structure between the stimulating and reference electrodes. The proposed dam structure is effective in maximizing interelectrode impedance. In particular, conducted experiments show that an interelectrode dam structure ranging from a few hundreds of nanometers to approximately two micrometers (~2 μm) increases ZAR by a substantial factor (e.g., ranging from 2-8×), which enables a minimization of the spacing s, resulting in a high-resolution, high focality stimulation.

As shown in FIGS. 8A and 8B, an electrode array of active electrodes A and reference electrodes R is arranged in a two-dimensional matrix in a first direction and a second direction. The electrode array may be implemented using low temperature polysilicon deposition which is compatible with complementary metal oxide semiconductor (CMOS) technology. Additionally, the electrode array shown in FIGS. 8A and 8B may be significantly scaled (e.g., up to 500 electrodes per $mm^2$), which allows the selective stimulation of thousands of electrogenic cells (such as neurons or cardiomyocytes) in parallel for furthering the study of neuronal networks. For example, the electrode array according can achieve high resolution (e.g., <80 μm in lateral current spread) neural stimulation, which enables high spatial selectivity (e.g., <100 μm).

In some implementations, metal coated BSi nanopatterned electrode of the electrode array achieve a desired electrical impedance (e.g., of <10 kΩ for a geometric area of 30×30 μm$^2$), which allows for low voltage evolution (e.g., $-0.6V<V_{stimulation}<0.8V$) during stimulation. In some implementations, the metal coated BSi nanopatterned electrode significantly increase the total 3D electrode surface area (e.g., from 2-10 times), therefore allowing for a drastic increase in charge density capacity. Additionally, the metal coated BSi nanopatterned electrodes limit biofouling over time, which limits the electrode increase in impedance to a maximum of 1 order of magnitude for instance from a pristine impedance of 10 kΩ to an impedance of 100 kΩ at 1 kHz after 1 month of implantation.

FIGS. 9A-9F illustrate a process for nanopattern fabrication of high-pressure sputtered black silicon (BSi) nanopatterned electrodes, according to various aspects of the present disclosure.

Figures 9A, 9B, 9C, 9D, 9E, 9F:
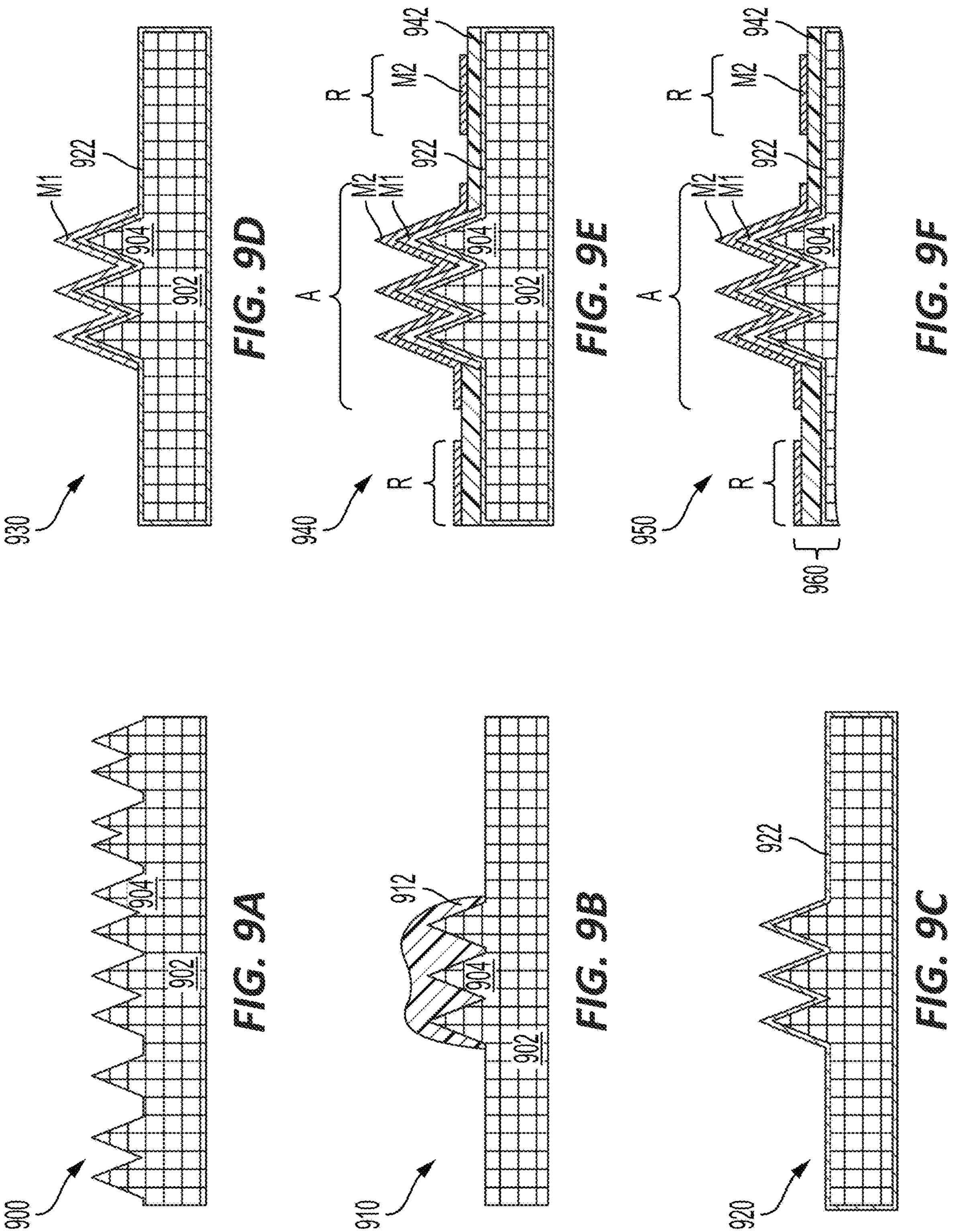
FIGS. 9A-9F illustrate a process for nanopatterned fabrication of high-pressure sputtered black silicon (BSi) nanopatterned electrodes, according to various aspects of the present disclosure.

As shown in FIG. 9A, at step 900, in which the nanopattern fabrication process begins by etching a wafer 902 (e.g., a silicon (Si)) in a mixture of sulfur hexafluoride ($SF_6$)/oxygen ($O_2$) gases at cryogenic temperatures (e.g., −110 °C-160 °C). The ratio of $SF_6$ to $O_2$ or chamber pressure or chamber temperature can be used to determine physical features 904 (e.g., a BSi nanopattern).

As shown in FIG. 9B, at step 910, after formation of the physical features 904, electrode definition and planarization are performed via photolithography and isotropic etching. For example, isotropic etching of the wafer 902 (e.g., an Si wafer) is achieved either via xenon difluoride ($XeF_2$) or high pressure inductively coupled plasma (ICP) $SF_6$ etching. This step is the most challenging in the fabrication process due to the difficulties related to applying and exposing a photoresist 912 on dense 3D features of the physical features 904.

As shown in FIG. 9C, at step 920, following electrode definition and planarization at step 920, the wafer 902 is oxidized in a tube furnace at predetermined temperatures (e.g., ranging from 1000 °C-1100 °C) to grow a thick (e.g., 100-1200 nm) oxide layer 922 that functions as the base insulator of the stimulating probe.

As shown in FIG. 9D, at step 930, a first conductive layer (e.g., a first metal layer (M1)), which defines channel traces, electrodes, and bonding pads, is patterned via photolithography. In this example, metal combinations including, but not limited to, Ti/Au, Ti/Pt, Ti/PtIr, Ti/Pt/Ir, Ti/Pt/IrOx, Ti/Ir, Ti/TiN, Ti/Pt/TiN, Ti/IrOx are sputter deposited on the physical features 904 to form the M1 metal layer.

As shown in FIG. 9E, at step 940, a liftoff process followed by plasma enhanced chemical vapor deposition (PECVD) (e.g., of ~150-700 nm) of a mixture layer (e.g., $Si_2N_3$ and $SiO_2$) for forming an isolation layer 942 that is employed to isolate the channels from each other and the traces from the environment. Additionally, photolithography is employed to reveal the active electrodes and bonding pads which will be etched to expose M1. Upon etching, another lithographic step is used to pattern a second metal (M2) layer, which defines the reference electrode R and produces a protruding active electrode A, which further decreases an electrode impedance $Z_e$.

As shown in FIG. 9F, at step 950, finally, a series of front and back dry etching can be employed to release a micro-probe 960 from the wafer 902. FIGS. 9A-9F illustrate fabrication of nano patterned electrodes (e.g., micro-probe 960) that enable formation of an implantable, free standing shank that contains multiple electrodes. The nano patterned electrodes (e.g., micro-probe 960) can be applied to a multi-channel device, such as a brain or spinal cord machine interface, as opposed to a free standing electrode, for example, according to the process shown in FIGS. 4A-4F.

FIGS. 10A-10G illustrate an alternative process for fabrication of high-pressure sputtered black silicon (BSi) nanopatterned electrodes to provide a free standing neural probe, according to various aspects of the present disclosure.

Figure 10A:
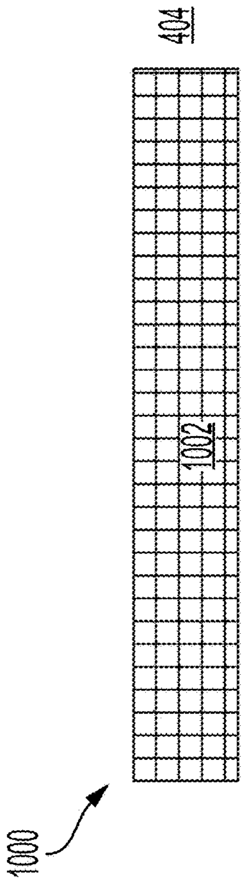
FIGS. 10A-10G illustrate an alternative process for fabrication of high-pressure sputtered black silicon (BSi) nanopatterned electrodes to provide a flat probe, according to various aspects of the present disclosure.
Figure 10B:
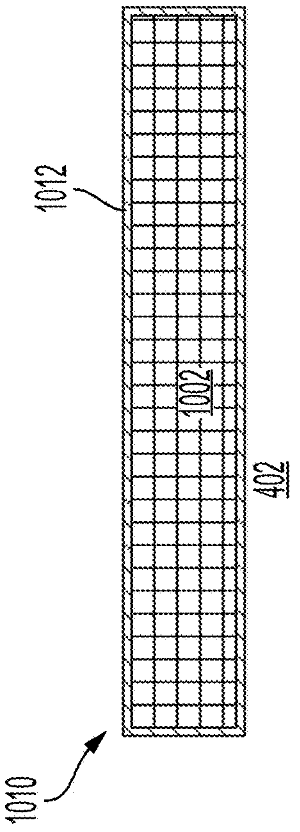
Figure 10C:
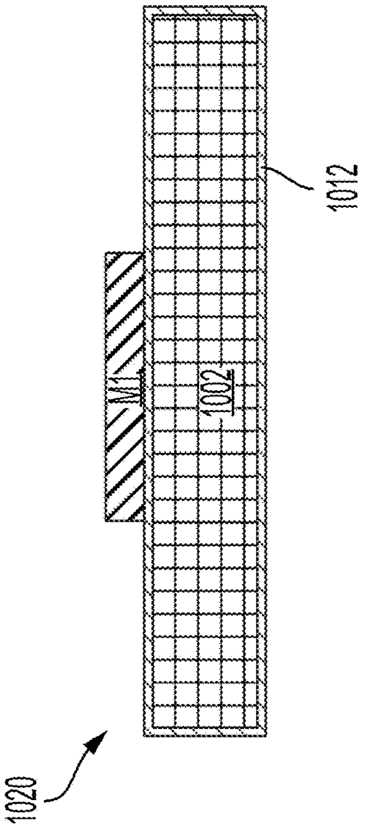
Figure 10D:
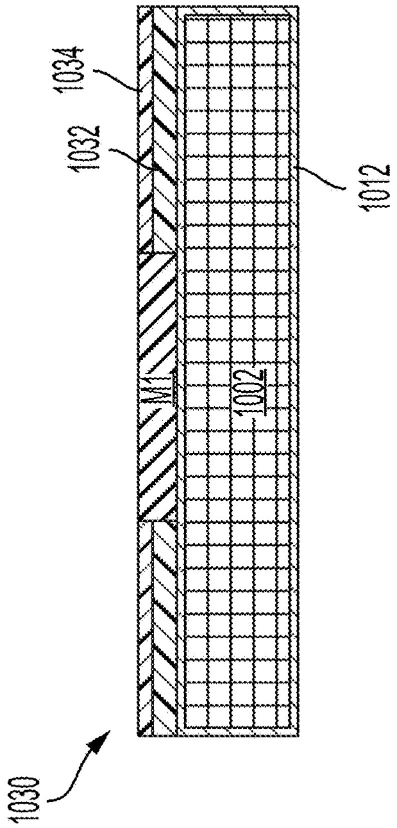

As shown in FIG. 10A, at step 1000, the alternative route is based on a free standing neural probe approach, which begins with a wafer 1002 (silicon (Si)). As shown in FIG. 10B, at step 1010, the wafer 1002 is oxidized to grow a thick (e.g., 100-1200 nm) oxide layer 1012 that functions as a base insulator of the flat probe. As shown in FIG. 10C, at step 1020, an M1 metal layer is patterned. As shown in FIG. 10D, at step 1030, insulating layers 1032,1034 (e.g., $Si_2N_3/SiO_2/HfO_2$) are applied and locations of the electrode array and bonding pads are revealed via dry etching.

Figure 10G:
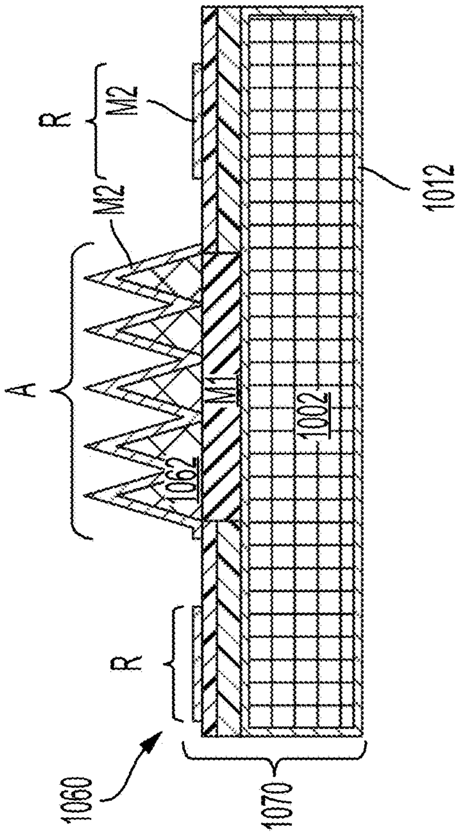
Figure 10E:
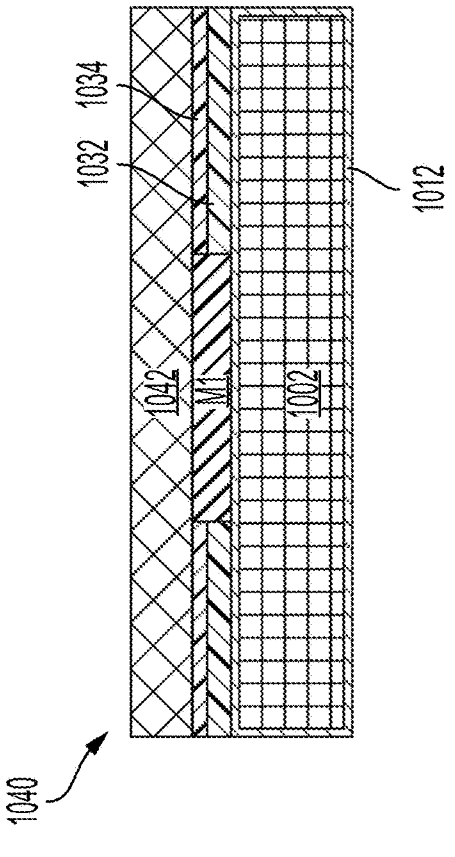
Figure 10F:
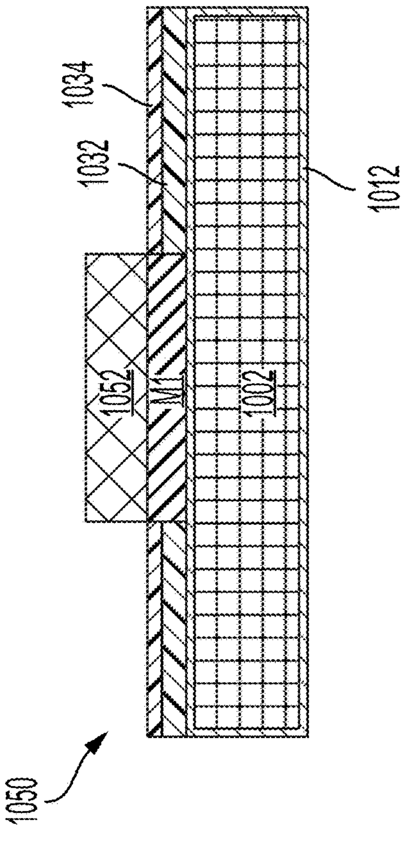

As shown in FIG. 10E, at step 1040, a blanket amorphous silicon 1042 (α-Si) deposition is applied, for example, via plasma enhanced chemical vapor deposition (PECVD), supporting, e-beam evaporation, or other like deposition technique. As shown in FIG. 10F, at step 1050, photolithography followed by dry etching is employed to remove the α-Si 1042 from the probe except for the electrode array location to form a patterned α-Si 1052.

As shown in FIG. 10F, following formation of the patterned α-Si 1052 at step 1040 of FIG. 10E, a cryogenic etching of the patterned α-Si 1052 forms BSi features 1062 in FIG. 10G on those areas where the patterned α-Si 1052 was not removed which coincides with the stimulating electrodes. Cryogenic etching is primarily chemical in nature, therefore, applying a thin layer (e.g., ~10 nm) of hafnium oxide ($HfO_2$) enables the BSi patterning without causing any damage to the rest of the probe. Alternatively, from step 1040 in FIG. 10E, a blanket cryogenic ($Sf6/O_2$) Etch can be performed to form BSi everywhere on the same in the same fashion, as shown in FIG. 9A. After BSi is formed everywhere, a lithographic step can be applied to protect the stimulating and reference electrodes in the same fashion, as shown in FIG. 9B.

As shown in FIG. 10G, at step 1060, photolithography and sputter deposition of a second conductive layer (e.g., a second metal layer (M2)) is employed to metallize the stimulating electrodes S and reference electrodes R to form a micro-sensor 1070. In some implementations, the a micro-sensor 1070 enables formation of a free standing neural probe, which may be composed of one (1) or multiple thin (30 um in thickness) shanks and a thicker (200 um) base that is used for handling the free standing neural probe.

Figure 11:
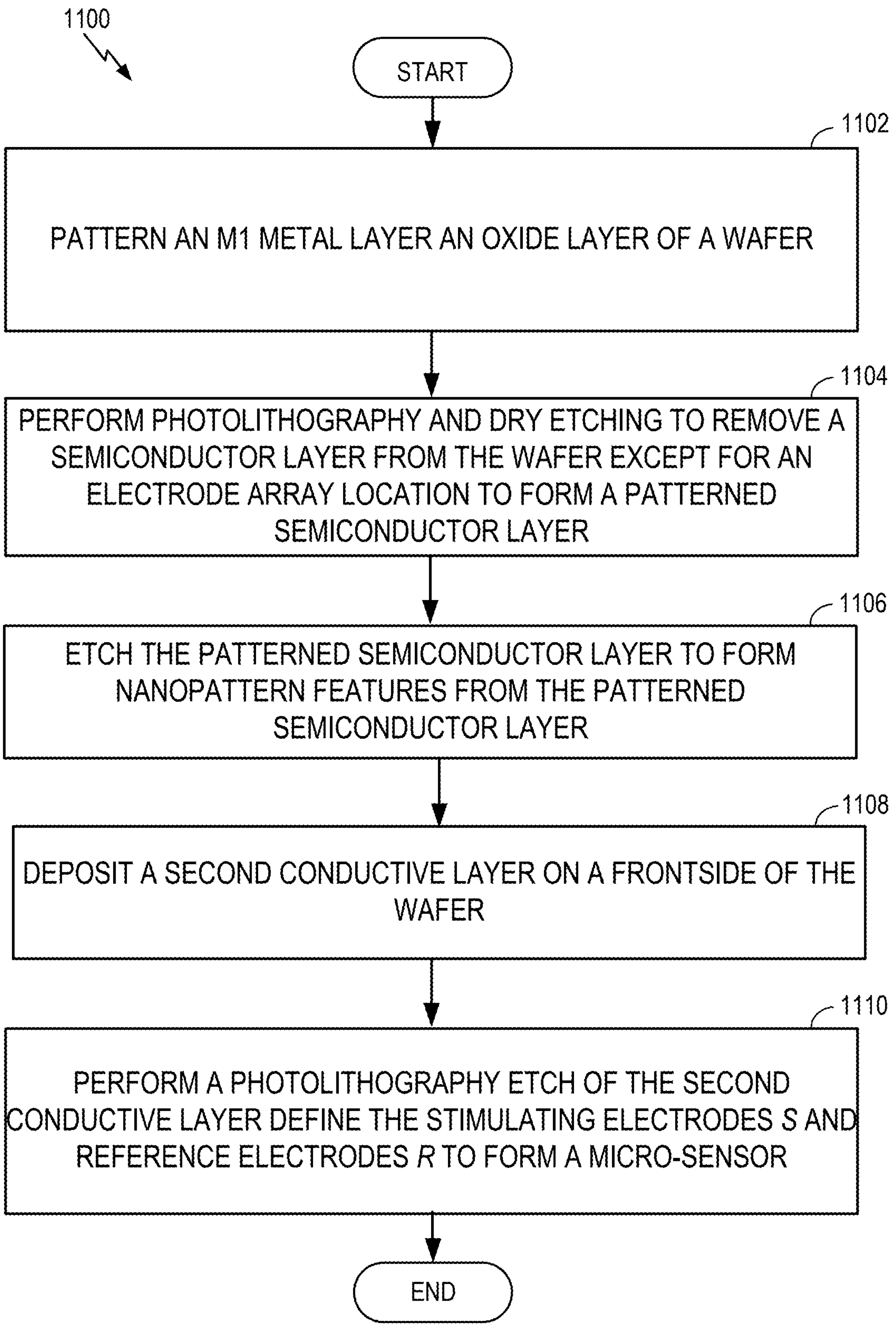
FIG. 11 is a flow chart illustrating a method for fabrication of high-pressure sputtered black silicon (BSi) nano-patterned electrodes, according to various aspects of the present disclosure.

FIG. 11 is a flow chart illustrating a method for fabrication of high-pressure sputtered black silicon (BSi) nano-patterned electrodes, according to various aspects of the present disclosure. A method 1100 begins at block 1102, in which an M1 metal layer is patterned an oxide layer of a wafer. For example, as shown in FIG. 10B, at step 1010, the wafer 1002 is oxidized to grow a thick (e.g., 100-1200 nm) oxide layer 1012 that functions as a base insulator of the flat probe. As shown in FIG. 10C, at step 1020, an M1 metal layer is patterned.

At block 1104, photolithography and dry etching is performed to remove a semiconductor layer from the wafer except for an electrode array location to form a patterned semiconductor layer. For example, as shown in FIG. 10E, at step 1040, a blanket amorphous silicon 1042 (α-Si) deposition is applied, for example, via plasma enhanced chemical vapor deposition (PECVD). As shown in FIG. 10F, at step 1050, photolithography followed by dry etching is employed to remove the α-Si 1042 from the probe except for the electrode array location to form a patterned α-Si 1052.

At block 1106, the patterned semiconductor layer is etched to form nanopattern features from the patterned semiconductor layer. For example, As shown in FIG. 10F, following formation of the patterned α-Si 1052 at step 1040 of FIG. 10E, a cryogenic etching of the patterned α-Si 1052 forms BSi features 1062 in FIG. 10G on those areas where the patterned α-Si 1052 was not removed which coincides with the stimulating electrodes. Cryogenic etching is primarily chemical in nature, therefore, applying a thin layer (e.g., ~10 nm) of hafnium oxide ($HfO_2$) enables the BSi patterning without causing any damage to the rest of the probe.

At block 1108, a second conductive layer is deposited on a frontside of the wafer. For example, as shown in FIG. 10G, at step 1060, sputter deposition of a second conductive layer (e.g., a second metal layer (M2)) is performed on the frontside of the wafer 1002 having the BSi features 1062. At block 1110, a photolithography etch performed on the second conductive layer to define the stimulating electrodes S and reference electrodes R to form a micro-sensor. For example, as shown as shown in FIG. 10G, at step 1060, a photolithography etch of the second metal layer (M2 is employed to define the stimulating electrodes S and reference electrodes R to form a micro-sensor 1070.

According to various aspects of the present disclosure, a fabrication process enables a substantial decrease electrode impedance, biofouling, and a distance between the target tissue and the electrode. This process increases a charge delivery capacity and charge injection limit, which enables application for both sensing electrodes and stimulation electrodes.

Although the present disclosure and its advantages have been described in detail, it should be understood that various changes, substitutions, and alterations can be made herein without departing from the technology of the present disclosure as defined by the appended claims. For example, relational terms, such as "above" and "below" are used with respect to a substrate or electronic device. Of course, if the substrate or electronic device is inverted, above becomes below, and vice versa. Additionally, if oriented sideways, above and below may refer to sides of a substrate or electronic device. Moreover, the scope of the present application is not intended to be limited to the particular configurations of the process, machine, manufacture, and composition of matter, means, methods, and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding configurations described herein may be utilized according to the present disclosure. Accordingly, the appended claims are intended to include within their scope such processes, machines, manufacture, compositions of matter, means, methods, or steps.

What is claimed is:

1. A sensor, comprising:

a substrate having a planar backside surface;

a nano-patterned semiconductor layer on a frontside of the substrate, wherein the nano-patterned semiconductor layer comprises black silicon (BSi) features;

a frontside conductive layer on the nano-patterned semiconductor layer on the frontside of the substrate, comprising a conductive material coating over the BSi features;

a backside conductive layer on the planar backside surface of the substrate, opposite from the frontside conductive layer;

a bonding layer on the backside conductive layer; and a cable coupled to the backside conductive layer through the bonding layer, the cable being distal from the frontside conductive layer.

2. The sensor of claim 1, in which the BSi features comprise nano-pillars and/or micro-pillars.

3. The sensor of claim 1, in which the nano-patterned semiconductor layer comprises dense conical BSi features.

4. The sensor of claim 1, in which the nano-patterned semiconductor layer comprises sparse conical BSi features.

5. The sensor of claim 1, in which the bonding layer comprises indium bumps or biocompatible paste.

6. The sensor of claim 1, further comprising an encapsulation layer on side walls of the sensor and a surface of the cable coupled to the backside conductive layer.

7. The sensor of claim 1, in which the frontside conductive layer is sputter-deposited and comprises one of titanium/gold (Ti/Au), titanium/platinum (Ti/Pt), titanium/platinum iridium (Ti/PtIr), titanium/platinum/iridium (Ti/Pt/Ir), titanium/platinum/iridium oxide (Ti/Pt/IrOx), titanium/iridium (Ti/Ir), titanium/titanium nitride (Ti/TiN), titanium/platinum/titanium nitride (Ti/Pt/TiN), and/or titanium/iridium oxide (Ti/IrOx).

8. The sensor of claim 1, in which the backside conductive layer comprises titanium/gold (Ti/Au) and/or titanium/platinum (Ti/Pt).

9. A sensor, comprising:

a substrate;

a nano-patterned semiconductor layer on a portion of a frontside of the substrate, wherein the nano-patterned semiconductor layer comprises black silicon (BSi) features;

a first conductive layer on the nano-patterned semiconductor layer on the portion of the frontside of the substrate, comprising a conductive material coating over the BSi features;

an isolation layer on the frontside of the substrate and surrounding the active electrode;

a first portion of a second conductive layer on the first conductive layer on the nano-patterned semiconductor layer to form an active electrode; and a second portion of the second conductive layer on the isolation substrate and surrounding the active electrode on the portion of the frontside of the substrate to form a reference electrode.

10. The sensor of claim 9, in which the BSi features comprise nano-pillars and/or micro-pillars.

11. The sensor of claim 9, in which the nano-patterned semiconductor layer comprises dense conical BSi features.

12. The sensor of claim 9, in which the nano-patterned semiconductor layer comprises sparse conical BSi features.

13. The sensor of claim 9, further comprising an oxide layer on the substrate and on the nano-patterned semiconductor layer.

14. The sensor of claim 9, in which the first conductive layer comprises a first metal layer (M1) and the second conductive layer comprises a second metal layer (M2).

* * * * *